United States Patent
Sierks et al.

(10) Patent No.: US 9,340,606 B2
(45) Date of Patent: May 17, 2016

(54) IMMUNIZATION WITH AMYLOID-BETA OLIGOMERS

(75) Inventors: Michael Sierks, Ft. McDowell, AZ (US); Srinath Kasturirangan, Germantown, MD (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 270 days.

(21) Appl. No.: 13/821,180

(22) PCT Filed: Oct. 26, 2011

(86) PCT No.: PCT/US2011/057904
§ 371 (c)(1),
(2), (4) Date: Mar. 6, 2013

(87) PCT Pub. No.: WO2012/082237
PCT Pub. Date: Jun. 21, 2012

(65) Prior Publication Data
US 2013/0287800 A1 Oct. 31, 2013

Related U.S. Application Data

(60) Provisional application No. 61/406,734, filed on Oct. 26, 2010, provisional application No. 61/406,728, filed on Oct. 26, 2010, provisional application No. 61/406,721, filed on Oct. 26, 2010.

(51) Int. Cl.
| | |
|---|---|
| *C07K 16/18* | (2006.01) |
| *G01N 33/68* | (2006.01) |
| *G01N 33/543* | (2006.01) |
| *A61K 38/17* | (2006.01) |
| *A61K 39/395* | (2006.01) |

(52) U.S. Cl.
CPC ............. *C07K 16/18* (2013.01); *A61K 38/1716* (2013.01); *A61K 39/3955* (2013.01); *G01N 33/5438* (2013.01); *G01N 33/54386* (2013.01); *G01N 33/6857* (2013.01); *G01N 33/6896* (2013.01)

(58) Field of Classification Search
None
See application file for complete search history.

(56) References Cited

U.S. PATENT DOCUMENTS

| | | |
|---|---|---|
| 8,124,076 B2 | 2/2012 | Solomon et al. |
| 8,409,411 B2 | 4/2013 | Prasad et al. |
| 8,507,206 B2 | 8/2013 | Lambert et al. |

(Continued)

FOREIGN PATENT DOCUMENTS

| | | |
|---|---|---|
| WO | WO2006014478 A1 | 2/2006 |
| WO | WO2007064972 A2 | 6/2007 |

(Continued)

OTHER PUBLICATIONS

Shi et al., Functional and Pharmacokinetic Properties of Antibody-Avidin Fusion Proteins. J Immunol. May 15, 1997;158(10):4797-804.*

(Continued)

*Primary Examiner* — Gregory S Emch
*Assistant Examiner* — Aurora M Fontainhas
(74) *Attorney, Agent, or Firm* — Viksnins Harris & Padys PLLP

(57) ABSTRACT

The present invention provides methods of immunization against Alzheimer's Disease and compositions for use in such methods.

12 Claims, 9 Drawing Sheets

(56) References Cited

U.S. PATENT DOCUMENTS

| | | |
|---|---|---|
| 2005/0003396 A1 | 1/2005 | Ozkan et al. |
| 2006/0105394 A1 | 5/2006 | Pomara |
| 2008/0113444 A1 | 5/2008 | Pray |
| 2009/0017197 A1 | 1/2009 | Zhang et al. |
| 2009/0081190 A1 | 3/2009 | Stassar et al. |
| 2010/0104577 A1 | 4/2010 | Golde et al. |

FOREIGN PATENT DOCUMENTS

| | | |
|---|---|---|
| WO | WO2008045962 A2 | 4/2008 |
| WO | WO2009004494 A2 | 1/2009 |
| WO | WO2009085200 A2 | 7/2009 |

OTHER PUBLICATIONS

Wang, Joseph, "Nanomaterial-based electrochemical biosensors," Analyst, Jan. 2005, pp. 421-426, vol. 130, No. 4.

Winblad, B., et al., "Mild cognitive impairment—beyond controversies, towards a consensus: report of the International Working Group on Mild Cognitive Impairment," J. Intern. Med., Sep. 2004, pp. 240-246, vol. 256, No. 3.

Wu, Huiping, et al., "Artificial Antibodies for Affinity Chromatography of Homologous Proteins: Application to Blood Clotting Proteins," Biotechnol. Prog., May-Jun. 1998, pp. 496-499, vol. 14, No. 3.

Wu, Huiping, et al., "Stepwise in vitro affinity maturation of Vitaxin, an alphav beta3- specific humanized mAb," Proc. Natl. Acad. Sci., May 1998, pp. 6037-6042, vol. 95, No. 11.

Yuan, Bin, et al., "Improved Affinity Selection of an scFv Antibody Fragment Against -amyloid Using Phage Display Technology and Off-rate Based Selection," Elec. J. Biotechnol., Apr. 2006, pp. 171-175, vol. 9, No. 2.

Zarranz, Juan J., et al., "The new mutation, E46K, of alpha-synuclein causes Parkinson and Lewy body dementia." Ann. Neurol., Feb. 2004, pp. 164-173, vol. 55, No. 2.

Zhou, Chun, et al., "A human single-chain Fv intrabody blocks aberrant cellular effects of overexpressed alpha-synuclein," Mol. Ther., Dec. 2004, pp. 1023-2031, vol. 10, No. 6.

Zhu, Min, et al., "The association of alpha-synuclein with membranes affects bilayer structure, stability, and fibril formation," J. Biol. Chem., Oct. 2003, pp. 40186-40197, vol. 278, No. 41.

Beach, Thomas G., et al., "Lamina-specific arrangement of astrocytic gliosis and senile plaques in Alzheimer's disease visual cortex," Brain Res., Nov. 1988, pp. 357-361, vol. 463, No. 2.

Adams, Gregory P., et al., "Highly specific in vivo tumor targeting by monovalent and divalent forms of 741F8 anti-c-erbB-2 single-chain Fv," Cancer Res., Sep. 1993, pp. 4026-4034, vol. 53, No. 17.

Barghorn, Stefan, et al., "Globular amyloid beta-peptide oligomer—a homogenous and stable neuropathological protein in Alzheimer's disease," J. Neurochem., Nov. 2005, pp. 834-847, vol. 95, No. 3.

Barkhordarian, Hedieh, et al., "Isolating recombinant antibodies against specific protein morphologies using atomic force microscopy and phage display technologies," Protein Eng. Des. Sel., 2006, pp. 497-502, vol. 19, No. 11.

Birmingham, Karen, et al., "Set back to Alzheimer vaccine studies," Nat. Med., Mar. 2002, pp. 199-200, vol. 8, No. 3.

Caughey, Byron, et al., "Protofibrils, pores, fibrils, and neurodegeneration: separating the responsible protein aggregates from the innocent bystanders," Annu. Rev. Neurosci., 2003, pp. 267-298, vol. 26.

Citron, Martin, "Strategies for disease modification in Alzheimer's disease," Nat. Rev. Neurosci., Sep. 2004, pp. 677-685, vol. 5, No. 9.

Cleary, James, et al., "Beta-amyloid(1-40) effects on behavior and memory," Brain Res., Jun. 1995, pp. 69-74, vol. 682, Nos. 1-2.

Cleary, James, et al., "Natural oligomers of the amyloid-beta protein specifically disrupt cognitive function," Nat. Neurosci., Jan. 2005, pp. 79-84, vol. 8, No. 1.

Colcher, David, et al., "In vivo tumor targeting of a recombinant single-chain antigen-binding protein," J. Natl. Cancer Inst., Jul. 1990, pp. 1191-1197, vol. 82, No. 14.

Dodart, Jean-Cosme, et al., "Immunization reverses memory deficits without reducing brain Abeta burden in Alzheimer's disease model," Nat. Neurosci., May 2002, pp. 452-457, vol. 5, No. 5.

Emadi, Sharareh, et al., "Isolation of a human single chain antibody fragment against oligomeric alpha-synuclein that inhibits aggregation and prevents alpha-synuclein-induced toxicity," J. Mol. Biol., May 2007, pp. 1132-1144, vol. 368, No. 4.

Emadi, Sharareh, et al., "Detecting morphologically distinct oligomeric forms of alpha-synuclein," Apr. 2009, J. Biol. Chem., pp. 11048-11058, vol. 284, No. 17.

Enya, Miho, et al., "Appearance of sodium dodecyl sulfate-stable amyloid beta-protein (Abeta) dimer in the cortex during aging," Am. J. Pathol., Jan. 1999, pp. 271-279, vol. 154, No. 1.

Estus, Steven, et al., Potentially Amyloidogenic, Carboxyl-Terminal Derivatives of the Amyloid Protein Precursor, Science, Feb. 1992, pp. 726-728, vol. 255, No. 5045.

Funato, Hiromasa, et al., "Presence of sodium dodecyl sulfate-stable amyloid beta-protein dimers in the hippocampus CA1 not exhibiting neurofibrillary tangle formation," Am. J. Pathol., Jul. 1999, pp. 23-28, vol. 155, No. 1.

Glabe, Charles G. "Common mechanisms of amyloid oligomer pathogenesis in degenerative disease," Neurobiol. Aging, Apr. 2006, pp. 570-575, vol. 27, No. 4.

Golde, Todd E., et al., "Processing of the Amyloid Protein Precursor to Potentially Amyloidogenic Derivatives," Science, Feb. 1992, pp. 728-730, vol. 255, No. 5045.

Gong, Yuesong, et al., "Alzheimer's disease-affected brain: presence of oligomeric A beta ligands (ADDLs) suggests a molecular basis for reversible memory loss," Proc. Natl. Acad. Sci., Sep. 2003, pp. 10417-10422, vol. 100, No. 18.

Haass, Christian, et al., "Soluble protein oligomers in neurodegeneration: lessons from the Alzheimer's amyloid beta-peptide," Nat. Rev. Mol. Cell Biol., Feb. 2007, pp. 101-112, vol. 8, No. 2.

Hardy, John A., et al., "Alzheimer's disease: the amyloid cascade hypothesis," Science, Apr. 1992, pp. 184-185, vol. 256, No. 5054.

Hardy, John A., et al., "The amyloid hypothesis of Alzheimer's disease: progress and problems on the road to therapeutics," Science, Jul. 2002, pp. 353-356, vol. 297, No. 5580.

Harper, James D., et al., "Models of amyloid seeding in Alzheimer's disease and Scrapie: mechanistic truths and physiological consequences of the time-dependent solubility of amyloid proteins," Annu. Rev. Biochem., 1997, pp. 385-407, vol. 66.

Harper, James D., et al., "Observation of metastable Aβ amyloid protofibrils by atomic force microscopy," Chem. Biol., Feb. 1997, pp. 119-125, vol. 4, No. 2.

Hock, Christoph, "Antibodies against beta-amyloid slow cognitive decline in Alzheimer's disease," Neuron, May 2003, pp. 547-554, vol. 38, No. 4.

Huston, James S., et al., "Medical applications of single-chain antibodies," Int. Rev. Immunol., 1993, pp. 195-217, vol. 10, No. 2-3.

Kang, Jie, et al., "The precursor of Alzheimer's disease amyloid A4 protein resembles a cell-surface receptor," Nature, Feb. 1987, pp. 733-736, vol. 325, No. 6106.

Kasturirangan, Srinath, et al., "Isolation and Characterization of Antibody Fragments Selective for Specific Protein Morphologies from Nanogram Antigen Samples," Biotechnol. Prog., 2013, pp. 463-471, vol. 29, No. 2.

Kawarabayashi, Takeshi, et al., "Dimeric amyloid beta protein rapidly accumulates in lipid rafts followed by apolipoprotein E and phosphorylated tau accumulation in the Tg2576 mouse model of Alzheimer's disease," J. Neurosci., Apr. 2004, pp. 3801-3809, vol. 24, No. 15.

Kayed, Rakez, et al., "Conformation-dependent anti-amyloid oligomer antibodies," Methods Enzymol., 2006, pp. 326-344, vol. 413.

Kotilinek, Linda A., et al., "Reversible memory loss in a mouse transgenic model of Alzheimer's disease," J. Neurosci., Aug. 2002, pp. 6331-6335, vol. 22, No. 15.

Lambert, Mary P., et al., "Diffusible, nonfibrillar ligands derived from Abeta1-42 are potent central nervous system neurotoxins," Proc. Natl. Acad. Sci., May 1998, pp. 6448-6453, vol. 95, No. 11.

(56) References Cited

OTHER PUBLICATIONS

Lambert, Mary P., et al., "Monoclonal antibodies that target pathological assemblies of Abeta," J. Neurochem., Jan. 2007, pp. 23-35, vol. 100, No. 1.
Lee, Chung-Chung, et al., "A three-stage kinetic model of amyloid fibrillation," Biophys. J., May 2007, pp. 3448-3458, vol. 92, No. 10.
Legrand, C., "Lactate dehydrogenase (LDH) activity of the cultured eukaryotic cells as marker of the number of dead cells in the medium [corrected]," J. Biotechnol., Sep. 1992, pp. 231-243, vol. 25, No. 3.
Lesne, Sylvain, et al., "A specific amyloid-beta protein assembly in the brain impairs memory," Nature, Mar. 2006, pp. 352-357, vol. 440, No. 7082.
Levine, Harry, "The challenge of inhibiting Abeta polymerization," Curr. Med. Chem., Jun. 2002, pp. 1121-1133, vol. 9, No. 11.
Levites, Yona, et al., "Anti-Abeta42- and anti-Abeta40-specific mAbs attenuate amyloid deposition in an Alzheimer disease mouse model," J. Clin. Invest., Jan. 2006, pp. 193-201, vol. 116, No. 1.
Liu, Ruitian, et al., "Single Chain Variable Fragments against β-Amyloid (Aβ) Can Inhibit Aβ Aggregation and Prevent Aβ-Induced Neurotoxicity," Biochem., 2004, pp. 6959-6967, vol. 43.
Lorenzo, Alfredo, et al., "Beta-amyloid neurotoxicity requires fibril formation and is inhibited by congo red," Proc. Natl. Acad. Sci., Dec. 1994, pp. 12243-12247, vol. 91, No. 25.
Marks, James D., et al., "By-passing immunization. Human antibodies from V-gene libraries displayed on phage," J. Mol. Biol., Dec. 1991, pp. 581-597, vol. 222, No. 3.
McDonald, Jessica M., et al., "The presence of sodium dodecyl sulphate-stable Abeta dimers is strongly associated with Alzheimer-type dementia," Brain, May 2010, pp. 1328-1341, vol. 133, Pt. 5.
McLean, Catriona A., "Soluble pool of Abeta amyloid as a determinant of severity of neurodegeneration in Alzheimer's disease," Ann. Neurol., Dec. 1999, pp. 860-866, vol. 46, No. 6.
Milenic, D.E., et al., "Construction, binding properties, metabolism, and tumor targeting of a single-chain Fv derived from the pancarcinoma monoclonal antibody CC49," Cancer Res., Dec. 1991, pp. 6363-6371, vol. 51, No. 23, Pt. 1.
Oddo, Salvatore, et al., "Triple-transgenic model of Alzheimer's disease with plaques and tangles: intracellular Abeta and synaptic dysfunction," Neuron, Jul. 2003, pp. 409-421, vol. 39, No. 3.
O'Hare, E., "Delayed behavioral effects following intrahippocampal injection of aggregated A beta (1-42)," Brain Res., Jan. 1999, pp. 1-10, vol. 815, No. 1.
Ono, Kenjiro, et al., "Structure-neurotoxicity relationships of amyloid beta-protein oligomers," Proc. Natl. Acad. Sci., Sep. 2009, pp. 14745-14750, vol. 106, No. 35.
Orgogozo, J.M., et al., "Subacute meningoencephalitis in a subset of patients with AD after Abeta42 immunization," Neurology, Jul. 2003, pp. 46-54, vol. 61, No. 1.
Pike, Christian J., "Neurodegeneration induced by beta-amyloid peptides in vitro: the role of peptide assembly state," J. Neurosci., Apr. 1993, pp. 1676-1687, vol. 13, No. 4.
Poirier, Michelle A., et al., "Huntingtin spheroids and protofibrils as precursors in polyglutamine fibrilization," J. Biol. Chem., Oct. 2002, pp. 41032-41037, vol. 277, No. 43.
Rafii, Michael S., et al., "Recent developments in Alzheimer's disease therapeutics," BMC Med., 2009, pp. 1-4, vol. 7, No. 7.
Roher, Alex E., "Morphology and toxicity of Abeta-(1-42) dimer derived from neuritic and vascular amyloid deposits of Alzheimer's disease," J. Biol. Chem., Aug. 1996, pp. 20631-20635, vol. 271, No. 34.
Sandberg, Anders, et al., "Stabilization of neurotoxic Alzheimer amyloid-beta Qligomers by protein," Proc. Nat. Acad. Sci., Aug. 2010, pp. 15595-15600, vol. 107, No. 35.
Schenk, Dale, "Amaloid-Beta immunotherapy for Alzheimer's disease: The end of the beginning," Nature, Oct. 2002, pp. 824-828, vol. 3.
Scherzinger, Eberhard, et al., "Self-assembly of polyglutamine-containing huntingtin fragments into amyloid-like fibrils: implications for Huntington's disease pathology," Proc. Natl. Acad. Sci., Apr. 1999, pp. 4604-4649, vol. 96, No. 8.
Selkoe, Dennis J., "Alzheimer's disease: genes, proteins, and therapy," Physiol. Rev., Apr. 2001, pp. 741-766, vol. 81, No. 2.
Shankar, Ganesh M., et al., "Natural oligomers of the Alzheimer amyloid-beta protein induce reversible synapse loss by modulating an NMDA-type glutamate receptor-dependent signaling pathway," J. Neurosci., Mar. 2007, pp. 2866-2875, vol. 27, No. 11.
Shankar, Ganesh M., et al., "Amyloid-beta protein dimers isolated directly from Alzheimer's brains impair synaptic plasticity and memory," Nat. Med., Aug. 2008, pp. 837-842, vol. 14, No. 8.
Sheets, Michael D., et al., "Efficient construction of a large nonimmune phage antibody library: the production of high-affinity human single-chain antibodies to protein antigens," Proc. Natl. Acad. Sci., Mar. 1998, pp. 6157-6162, vol. 95, No. 11.
Stains, Cliff I., et al., "Molecules that Target beta-Amyloid," Chem. Med. Chem., 2007, pp. 1674-1692, vol. 2.
Walsh, Dominic M., "The oligomerization of amyloid beta-protein begins intracellularly in cells derived from human brain," Biochemistry, 2000, pp. 10831-10839, vol. 39, No. 35.
Walsh, Dominic M., "Naturally secreted oligomers of amyloid beta protein potently inhibit hippocampal long-term potentiation in vivo," Nature, Apr. 2002, pp. 535-539, vol. 416, No. 6880.
Walsh, Dominic M., et al., "The role of cell-derived oligomers of Abeta in Alzheimer's disease and avenues for therapeutic intervention," Biochem. Soc. Trans., Nov. 2005, pp. 1087-1090, vol. 33, Pt. 5.
Wang, Min S., et al., "Characterizing antibody specificity to different protein morphologies by AFM," Langmuir, Jan. 2009, pp. 912-918, vol. 25, No. 2.
Wolfe, Michael S., "Therapeutic strategies for Alzheimer's disease," Nat. Rev. Drug Discov., Nov. 2002, pp. 859-866, vol. 1, No. 11.
Yankner, Bruce A., "Mechanisms of Neuronal Degeneration in Alzheimer's Disease," Neuron, May 1996, pp. 921-923, vol. 16.
Yokota, Takashi, et al., "Rapid tumor penetration of a single-chain Fv and comparison with other immunoglobulin forms," Cancer Res., Jun. 1992, pp. 3402-3408, vol. 52, No. 12.
Zameer, Andleeb, et al., "Single chain Fv antibodies against the 25-35 Abeta fragment inhibit aggregation and toxicity of Abeta42," Biochemistry, Sep. 2006, pp. 11532-11539, vol. 45, No. 38.
Zameer, Andleeb, et al., "Anti-oligomeric Aβ Single-chain Variable Domain Antibody Blocks Aβ-induced Toxicity Against Human Neuroblastoma Cells," J. Mol. Biol., Dec. 2008, pp. 917-928, vol. 384, No. 4.
International Search Report and Written Opinion for PCT/US2011/057904, mailed Apr. 6, 2012 (10 pages).
International Preliminary Report on Patentability for PCT/US2011/057904, mailed May 10, 2013 (6 pages).
Callaway, Ewen, "Alzheimer's drugs take a new tack," Nature, Sep. 2012, pp. 13-14, vol. 489.
Cobb, Nathan J., et al, "Prion diseases and their biochemical mechanisms," Biochemistry, 2009, pp. 2574-2585, vol. 48, No. 12.
Demarest, Stephen J., et al., "Antibody therapeutics, antibody engineering, and the merits of protein stability," Curr. Opin. Drug Discov. Dev., Sep. 2008, pp. 675-687, vol. 11, No. 5.
Elbakri, Ali, et al., "The state of antibody therapy," Hum. Immunol., Dec. 2010, pp. 1243-1250, vol. 71, No. 12.
Hudson, Peter J., et al., "Engineered antibodies," Nat. Med., 2003, pp. 129-134, vol. 9.
Jain, Maneesh, et al., "Engineering antibodies for clinical applications," Trends Biotechnol., Jul. 2007, pp. 307-316, vol. 25, No. 7.
Kang, Christine K., et al., "Identification of peptides that specifically bind Aβ1-40 amyloid in vitro and amyloid plaques in Alzheimer's disease brain using phage display," Neurobiol. Disease, 2003, pp. 146-156, vol. 14.
Kasturirangan, Srinath, et al., "Nanobody specific for oligomeric beta-amyloid stabilizes non-toxic form," Neurobiol. Aging, Jul. 2012, pp. 1320-1328, vol. 33, No. 7.
Lafaye, Pierre, et al., "Single-domain antibodies recognize selectively small oligomeric forms of amyloid β, prevent Aβ-induced neurotoxicity and inhibit fibril formation," Mol. Immunol., 2009, pp. 695-704, vol. 46.
Lemere, Cynthia A., et al., "Can Alzheimer disease be prevented by amyloid-beta immunotherapy?" Nat. Rev. Neurol., Feb. 2010, pp. 108-119, vol. 6, No. 2.

(56) References Cited

OTHER PUBLICATIONS

Liu, Ruitian, et al., "P4-354 Anti Beta-amyloid SCFV Inhibits ABeta Aggregation and Neurotoxicity," Neurobiol. Aging, 2004, pp. S575-S576, vol. 25, Supp. 2, Abstract.
Manoutcharian, K., et al., "Amyloid-beta peptide-specific single chain Fv antibodies isolated from an immune phage display library," J. Neuroimmunol., 2003, pp. 12-17, vol. 145.
Marcus, W.D., et al., "Characterization of an antibody scFv that recognizes fibrillar insulin and beta-amyloid using Atomic Force Microscopy," Nanomedicine, Mar. 2008, pp. 1-7, vol. 4, No. 1.
Mazzucchelli, Luca, et al., "Cell-Specific Peptide Binding by Human Neutrophils," Blood, Mar. 1999, pp. 1738-1748, vol. 93, No. 5.
Medecigo, M., et al., "Novel amyloid-beta specific scFv and VH antibody fragments from human and mouse phage display antibody libraries," J. Neuroimmunol., 2010, pp. 104-114, vol. 223.
Meli, Giovanni, et al., "Direct in Vivo Intracellular Selection of Conformation-sensitive Antibody Domains Targeting Alzheimer's Amyloid-β Oligomers," J. Mol. Biol., 2009, pp. 584-606, vol. 387.
Panza, Francesco, et al., "Immunotherapy for Alzheimer's disease: from anti-beta-amyloid to tau-based immunization strategies," Immunotherapy, Feb. 2012, pp. 213-238, vol. 4, No. 2.
Popkov, Mikhail, et al., "Isolation of human prostate cancer cell reactive antibodies using phage display technology," J. Immunol. Methods, 2004, pp. 137-151, vol. 291.
Rangan, Srinath Kasturi, et al., "Degradation of β-Amyloid by Proteolytic Antibody Light Chains," Biochem., 2003, pp. 14328-14334, vol. 42.
Santos, Alexander N., et al., "Amyloid-beta oligomers in cerebrospinal fluid are associated with cognitive decline in patients with Alzheimer's disease," J. Alzheimers Dis., 2012, pp. 171-176 vol. 29, No. 1.
Shlyakhtenko, Luda S., et al., "Single-molecule selection and recovery of structure-specific antibodies using atomic force microscopy," Nanomedicine, Sep. 2007, pp. 192-197, vol. 3, No. 3.
Sierks, Michael R., et al., "CSF Levels of oligomeric alpha-synuclein and beta-amyloid as biomarkers for neurodegenerative disease," Integr. Biol., Dec. 2011, pp. 1188-1196, vol. 3, No. 12.
Solomon, Beka, "Active immunization Alzheimer's Beta-amyloid peptide using phage display technology," Vaccine, 2007, pp. 3053-3056, vol. 25.
Solomon, Beka, "Immunological Approaches for Amyloid-beta Clearance Toward Treatment for Alzheimer's Disease," Rejuvenation Res., 2008, pp. 349-357, vol. 11, No. 2.
Von Bernhardi, Rommy, "Immunotherapy in Alzheimer's Disease: Where Do We Stand? Where Should We Go?" J. Alz. Disease, 2010, pp. 405-421, vol. 19.
Wang, Xiao-Ping, et al., "Conformation-dependent single-chain variable fragment antibodies specifically recognize beta-amyloid oligomers," FEBS Lett., 2009, pp. 579-584, vol. 583.
Yoshihara, Tomoki, et al., "Immunoreactivity of Phage Library-derived Human Single-Chain Antibodies to Amyloid Beta Conformers In Vitro," J. Biochem., 2008, pp. 475-486, vol. 143.
Yue, Shen, et al., "The toxicity of β-amyloid is attenuated by interaction with its specific human scFv E3 in vitro," Life Sciences, 2008, pp. 1249-1255, vol. 82.
Bothara, Manish, et al., "Nanomonitors: electrical immunoassays for protein biomarker profiling", Nanomedicine, 2008, pp. 423-436, vol. 3, No. 4.
Reddy, Ravikiran K., et al, "Nanomonitors: Protein Biosensors for Rapid Analyte Analysis," IEEE Sensors J., Jun. 2008, pp. 720-723, vol. 8, No. 6.
Venkatraman, Vinu L., et al., "Iridium oxide nanomonitors: Clinical diagnostic devices for health monitoring systems," Biosens. Bioelectron., Jun. 2009, pp. 3078-3083, vol. 24, No. 10.
Yang, Liju, et al., "AFM and impedance spectroscopy characterization of the immobilization of antibodies on indium-tin oxide electrode through self-assembled monolayer of epoxysilane and their capture of Escherichia coli O157:H7," Biosens. Bioelectron., Jan. 2005, pp. 1407-1416, vol. 20, No. 7.
NANOSENS, Product page for Nanoproducts, available at www.nanosens.nl/product.htm, 2005.
International Search Report and Written Opinion for PCT/US2011/057877, mailed May 2, 2012 (15 pages).
International Preliminary Report on Patentability for PCT/US2011/057877, mailed May 10, 2013 (10 pages).
International Search Report and Written Opinion for PCT/US2011/057925, mailed Feb. 15, 2012 (12 pages).
International Preliminary Report on Patentability for PCT/US2011/057925, mailed May 10, 2013 (8 pages).
Kasturirangan, Srinath, et al. "Engineered proteolytic nanobodies reduce Abeta burden and ameliorate Abeta-induced cytotoxicity," Biochemistry, Jun. 2010, pp. 4501-4508, vol. 49, No. 21.
Baxter, Leslie C., et al., "Apolipoprotein E epsilon 4 affects new learning in cognitively normal individuals at risk for Alzheimer's disease," Neurobiol. Aging, Nov. 2003, pp. 947-952, vol. 24, No. 7.
Beach, Thomas G., et al., "Perfusion-fixation of the human brain for immunohistochemistry: comparison with immersion-fixation," J. Neurosci. Methods, Mar. 1987, pp. 183-192, vol. 19, No. 3.
Beach, Thomas G., et al., "Patterns of gliosis in Alzheimer's disease and aging cerebrum," Glia, 1989, pp. 420-436, vol. 2, No. 6.
Beach, Thomas G., et al., "Senile plaques, amyloid beta-protein, and acetylcholinesterase fibres: laminar distributions in Alzheimer's disease striate cortex," Acta Neuropathol., 1992, pp. 292-299, vol. 83, No. 3.
Beach, Thomas G., et al., "The cholinergic deficit coincides with Abeta deposition at the earliest histopathologic stages of Alzheimer disease," J. Neuropathol. Exp. Neurol., Apr. 2000, pp. 308-813, vol. 59, No. 4.
Beach, Thomas G., et al., "Circle of Willis atherosclerosis: association with Alzheimer's disease, neuritic plaques and neurofibrillary tangles," Acta Neuropathol., Jan. 2007, pp. 13-21, vol. 113, No. 1.
Beach, Thomas G., "Physiologic origins of age-related beta-amyloid deposition," Neurodegener. Dis., 2008, pp. 143-145, vol. 5, Nos. 3-4.
Beach, Thomas G., et al., "The Sun Health Research Institute Brain Donation Program: Description and Experience, 1987-2007," Cell Tissue Bank, Sep. 2008, pp. 229-245, vol. 9, No. 3.
Beach, Thomas G., et al., "Evaluation of alpha-synuclein immunohistochemical methods used by invited experts." Acta Neuropathol., Sep. 2008, pp. 277-288, vol. 116, No. 3.
Blennow, Kaj., et al., "Cerebrospinal fluid and plasma biomarkers in Alzheimer disease," Nat. Rev. Neurol., Mar. 2010, pp. 131-144, vol. 6, No. 3.
Boder, Eric T., et al., "Directed evolution of antibody fragments with monovalent femtomolar antigen-binding affinity," Proc. Natl. Acad. Sci., 2000, pp. 10701-10705, vol. 97, No. 20.
Braak, H. and E. Braak, "Neuropathological stageing of Alzheimer-related changes," Acta Neuropathol., 1991, pp. 239-259, vol. 82, No. 4.
Braak, H., et al., "Evolution of neuronal changes in the course of Alzheimer's disease" J. Neural. Transm. Suppl., 1998, pp. 127-140, vol. 53.
Caselli, Richard J., et al., "Preclinical memory decline in cognitively normal apolipoprotein E epsilon4 homozygotes," Neurology, Jul. 1999, pp. 201-207, vol. 53, No. 1.
Caselli, Richard J., et al., "Preclinical cognitive decline in late middle-aged asymptomatic apolipoprotein E-e4/4 homozygotes: a replication study," J. Neurol. Sci., Aug. 2001, pp. 93-98, vol. 189, Nos. 1-2.
Caselli, Richard J., et al., "A distinctive interaction between memory and chronic daytime somnolence in asymptomatic APOE e4 homozygotes," Sleep, Jun. 2002, pp. 437-443, vol. 25, No. 4.
Caselli, Richard J., et al., "A distinctive interaction between chronic anxiety and problem solving in asymptomatic APOE e4 homozygotes," J. Neuropsychiatry Clin. Neurosci., Summer 2004, pp. 320-329, vol. 16, No. 3.
Caselli, Richard J., et al., "Longitudinal changes in cognition and behavior in asymptomatic carriers of the APOE e4 allele," Neurology, Jun. 2004, pp. 1990-1995, vol. 62, No. 11.
Cedazo-Minguez, Angel, et al., "Biomarkers for Alzheimer's disease and other forms of dementia: clinical needs, limitations and future aspects," Exp. Gerontol., Jan. 2010, pp. 5-14, vol. 45. No. 1.

(56) References Cited

OTHER PUBLICATIONS

Chang, Lei, et al., "Femtomole immunodetection of synthetic and endogenous amyloid-beta oligomers and its application to Alzheimer's disease drug candidate screening," J. Mol. Neurosci., 2003, pp. 305-313, vol. 20, No. 3.
Chowdhury, Partha S., et al., "Improving antibody affinity by mimicking somatic hypermutation in vitro," Nat. Biotechnol., Jun. 1999, pp. 568-572, vol. 17, No. 6.
Conway, Kelly A., et al., "Accelerated in vitro fibril formation by a mutant alpha-synuclein linked to early-onset Parkinson disease," Nat. Med., Nov. 1998, pp. 1318-1320, vol. 4, No. 11.
Conway, Kelly A., et al., "Acceleration of oligomerization, not fibrillization, is a shared property of both alpha-synuclein mutations linked to early-onset Parkinson's disease: implications for pathogenesis and therapy," Proc. Natl. Acad. Sci., Jan. 2000, pp. 571-576, vol. 97, No. 2.
Conway, Kelly A., et al., "Fibrils formed in vitro from alphasynuclein and two mutant forms linked to Parkinson's disease are typical amyloid," Biochemistry, Mar. 2000, pp. 2552-2563, vol. 39.
Conway, Kelly A., et al., "Kinetic stabilization of the alpha-synuclein protofibril by a dopamine- alpha-synuclein adduct," Science, Nov. 2001, pp. 1346-1349, vol. 294, No. 5545.
Crowley, Timothy A., et al., "Isolation of plasma from whole blood using planar microfiltersfor lab-on-a-chip applications," Lab Chip, Sep. 2005, pp. 922-929, vol. 5, No. 9.
Crowther, R. Anthony, et al., "Synthetic filaments assembled from C-terminally truncated alpha-synuclein," FEBS Lett, Oct. 1998, pp. 309-312, vol. 436, No. 3.
Danzer, Karin M., et al., "Different species of alpha-synuclein oligomers induce calcium influx and seeding," J. Neurosci., Aug. 2007, pp. 9220-9232, vol. 27, No. 34.
Dickson, Dennis W., "Required techniques and useful molecular markers in the neuropathologic diagnosis of neurodegenerative diseases," Acta Neuropathol., Jan. 2005, pp. 14-24, vol. 109, No. 1.
El-Agnaf, Omar M., et al., "Detection of oligomeric forms of alpha-synuclein protein in human plasma as a potential biomarker for Parkinson's disease," FASEB. J., Mar. 2006, pp. 419-425, vol. 20, No. 3.
Emadi Sharareh, et al., "Inhibiting Aggregation of alpha-Synuclein with Human Single Chain Antibody Fragments," Biochemistry, Mar. 2004, pp. 2871-2878, vol. 43, No. 10.
Formichi, Patrizia, et al., "Cerebrospinal fluid tau, A beta, and phosphorylated tau protein for the diagnosis of Alzheimer's disease." J. Cell Physiol., Jul. 2006, pp. 39-46, vol. 208, No. 1.
Friedhoff, Peter, et al., "Rapid assembly of Alzheimer-like paired helical filaments from microtubule-associated protein tau monitored by fluorescence in solution," Biochemistry, Jul. 1998, pp. 10223-10230, vol. 37, No. 28.
Garcia-Sierra, Francisco, et al., "Conformational changes and truncation of tau protein during tangle evolution in Alzheimer's disease," J. Alzheimers Dis., Apr. 2003, pp. 65-77, vol. 5, No. 2.
Georganopoulou, Dimitra G., et al., "Nanoparticle-based detection in cerebral spinal fluid of a soluble pathogenic biomarker for Alzheimer's disease," Proc. Natl. Acad. Sci., Feb. 2005, pp. 2273-2276, vol. 102, No. 7.
Ghoshal, Nupur, et al., "Tau conformational changes correspond to impairments of episodic memory in mild cognitive impairment and Alzheimer's disease," Exp. Neurol., Oct. 2002, pp. 475-493, vol. 177, No. 2.
Giasson, Benoit I., et al., "Mutant and wild type human alpha-synucleins assemble into elongated filaments with distinct morphologies in vitro," J. Biol. Chem., Mar. 1999, pp. 7619-7622, vol. 274, No. 12.
Giasson, Benoit I., et al., "Oxidative Damage Linked to Neurodegeneration by Selective Alpha-Synuclein Nitration in Synucleinopathy Lesions", Science, Nov. 2000, pp. 985-989, vol. 290.
Goedert, Michel, et al., "Tau proteins of Alzheimer paired helical filaments: abnormal phosphorylation of all six brain isoforms," Neuron, Jan. 1992, pp. 159-168, vol. 8, No. 1.

Goedert, Michel, "Alpha-synuclein and neurodegenerative diseases," Nat. Rev. Neurosci., Jul. 2001, pp. 492-501, vol. 2, No. 7.
Grundke-Iqbal, Inge, et al., "Abnormal phosphorylation of the microtubule-associated protein 15 tau (tau) in Alzheimer cytoskeletal pathology." Proc. Natl. Acad. Sci., Jul. 1986, pp. 4913-4917, vol. 83, No. 13.
Hasegawa, Masato, et al., "Alzheimer-like changes in microtubule-associated protein Tau induced by sulfated glycosaminoglycans. Inhibition of microtubule binding, stimulation of phosphorylation, and filament assembly depend on the degree of sulfation," J. Biol. Chem., Dec. 1997, pp. 33118-33124, vol. 272, No. 52.
Hohl, Ursula, et al., "Diagnostic accuracy of dementia with Lewy bodies," Arch. Neurol., Mar. 2000, pp. 347-351, vol. 57, No. 3.
Irving, Robert A., et al., "Affinity maturation of recombinant antibodies using E. coli mutator cells," Immunotechnology, Jun. 1996, pp. 127-143, vol. 2, No. 2.
Jackson, Jeffrey R., et al., "In vitro antibody maturation. Improvement of a high affinity, neutralizing antibody against IL-I beta," J. Immunol., Apr. 1995, pp. 3310-3019, vol. 154, No. 7.
Joachim, C. L., et al., "Clinically diagnosed Alzheimer's disease: autopsy results in 150 cases," Ann. Neurol., Jul. 1988, pp. 50-56, vol. 24, No. 1.
Kim, Tae-Wan, et al., "Presenilins and Alzheimer's disease." Current Opinion in Neurobiology, 1997, pp. 683-688, vol. 7, No. 5.
Klein, William L., "Synaptic targeting by Abeta oligomers (ADDLS) as a basis for memory loss in early Alzheimer's disease," Alzheimers Dement., Jan. 2006, pp. 43-55, vol. 2, No. 1.
Knopman, D.S., et al., "Neuropathology of cognitively normal elderly," J. Neuropathol. Exp. Neurol., Nov. 2003, pp. 1087-1095, vol. 62, No. 11.
Koffie, Robert M., et al., "Oligomeric amyloid beta associates with postsynaptic densities and correlates with excitatory synapse loss near senile plaques," Proc. Natl. Acad. Sci., Mar. 2009, pp. 4012-4017, vol. 106, No. 10.
Kosunen, O., et al., "Diagnostic accuracy of Alzheimer's disease: a neuropathological study," Acta. Neuropathol. (Berl), 1996, pp. 185-193, vol. 91, No. 2.
Lashuel, Hilal A., et al., "Alpha-Synuclein, Especially the Parkinson's Disease-associated Mutants, Forms Pore-like Annular and Tubular Protofibrils," J. Mol. Biol., Oct. 2002, pp. 1089-1102, vol. 322, No. 5.
Levicky, Rastislav, et al., "Using self-assembly to control the structure of DNA monolayers on gold: A neutron reflectivity study," J. Am. Chem. Soc., 1998, pp. 9787-9792, vol. 120, No. 38.
Liu, Chang-Wei, et al., "A precipitating role for truncated alpha-synuclein and the proteasome in alpha-synuclein aggregation: implications for pathogenesis of Parkinson disease," J. Biol. Chem., Jun. 2005, pp. 22670-22678, vol. 280, No. 24.
Liu, Ruitian, et al., "Residues 17-20 and 30-35 of beta-amyloid play critical roles in aggregation," J. Neurosci. Res., Jan. 2004, pp. 162-171, vol. 75, No. 2.
Liu, Ruitian, et al "Proteolytic antibody light chains alter beta-amyloid aggregation and prevent cytotoxicity," Biochemistry, Aug. 2004, pp. 9999-10007, vol. 43, No. 31.
Liu, Ruitian, et al., "Trehalose Differentially Inhibits Aggregation and Neurotoxicity of Betaamyloid 40 and 42," Neurobiol. Dis., Oct. 2005, pp. 74-81, vol. 20, No. 1.
Lue, Lih-Fen, et al., "Soluble amyloid beta peptide concentration as a predictor of synaptic change in Alzheimer's . disease," Am. J. Pathol., Sep. 1999, pp. 853-862, vol. 155, No. 3.
Maeda, Sumihiro, et al., "Increased levels of granular tau oligomers: an early sign of brain aging and Alzheimer's disease," Neurosci. Res., Mar. 2006, pp. 197-201, vol. 54, No. 3.
Marcus, W.D., et al., "Isolation of an scFv targeting BRG 1 using phage display with characterization by AFM," Biochem. Biophys. Res. Commun., Apr. 2006, pp. 1123-1129, vol. 342, No. 4.
Mattsson, Niklas, et al., "CSF biomarkers and incipient Alzheimer disease in patients with mild cognitive impairment," JAMA, Jul. 2009, pp. 385-393, vol. 302, No. 4.
McKeith, I.G., "Clinical Lewy body syndromes," Ann. N. Y. Acad. Sci., 2000, pp. 1-8, vol. 920.
McKhann, Guy, et al., "Clinical diagnosis of Alzheimer's disease: Report of the NINCDS-ADRDA Work Group under the auspices of

(56) References Cited

OTHER PUBLICATIONS

Department of Health and Human Services Task Force on Alzheimer's Disease," Neurology, Jul. 1984, pp. 939-944, vol. 34, No. 7.

Mezey, E., et al., "Alpha synuclein is present in Lewy bodies in sporadic Parkinson's disease," Mol. Psychiatry, Nov. 1998, pp. 493-499, vol. 3, No. 6.

Mirra, S.S., et al., "The Consortium to Establish a Registry for Alzheimer's Disease (CERAD). Part II Standardization of the neuropathologic assessment of Alzheimer's disease," Neurology, Apr. 1991, pp. 479-486, vol. 41, No. 4.

Murray, Ian V., et al., "Role of alpha-synuclein carboxy-terminus on fibril formation in vitro," Biochemistry, Jul. 2003, pp. 8530-8540, vol. 42, No. 28.

Narhi, Linda, et al., "Both familial Parkinson's disease mutations accelerate alpha-synuclein aggregation," J. Biol. Chem., Apr. 1999, pp. 9843-9846, vol. 274, No. 14.

Olsen, Mark J., et al., "Function-based isolation of novel enzymes from a large library," Nat. Biotechnol., Oct. 2000, pp. 1071-1074, vol. 18, No. 10.

Outeiro, Tiago Fleming, et al., "Formation of toxic oligomeric alpha-synuclein species in living cells," PLoS ONE, Apr. 2008, p. e1867, vol. 3, No. 4.

Periquet, Magali, et al., "Aggregated alpha-synuclein mediates dopaminergic neurotoxicity in vivo," J. Neurosci., Mar. 2007, pp. 3338-3346, vol. 27, No. 12.

Petersen, Ronald C., et al., "Mild cognitive impairment: clinical characterization and outcome," Arch. Neurol., Mar. 1999, pp. 303-308, vol. 56, No. 3.

Petersen, Ronald C., et al., "Practice parameter: early detection of dementia: mild cognitive impairment (an evidence-based review). Report of the Quality Standards Subcommittee of the American Academy of Neurology," Neurology, May 2001, pp. 1133-1142, vol. 56, No. 9.

Petersen, Ronald C., et al., "Current concepts in mild cognitive impairment," Arch. Neurol., Dec. 2001, pp. 1985-1992, vol. 58, No. 12.

Quintero-Hernandez, Veronica, et al., "The change of the scFv into the Fab format improves the stability and in vivo toxin neutralization capacity of recombinant antibodies," Mol. Immunol., Feb. 2007, pp. 1307-1315, vol. 44, No. 6.

Roher, Alex E., et al., "Proteomics-derived cerebrospinal fluid markers of autopsy-confirmed Alzheimer's disease," Biomarkers, Nov. 2009, pp. 493-501, vol. 14, No. 7.

Schier, Robert, et al., "Isolation of picomolar affinity anti-c-erbB-2 single-chain Fv by molecular evolution of the complementarity determining regions in the center of the antibody binding site," J. Mol. Biol., Nov. 1996, pp. 551-567, vol. 263, No. 4.

Schweers, Olaf, et al., "Structural studies of tau protein and Alzheimer paired helical filaments show no evidence for beta-structure," J. Biol. Chem., Sep. 1994, pp. 24290-24297, vol. 269, No. 39.

Selkoe, Dennis J., "Translating cell biology into therapeutic advances in Alzheimer's disease," Nature, Jun. 1999, pp. A23-A31, vol. 399.

Selkoe, Dennis J., "Toward a comprehensive theory for Alzheimer's disease. Hypothesis: Alzheimer's disease is caused by the cerebral accumulation and cytotoxicity of amyloid beta-protein," Ann. N. Y. Acad. Sci., 2000, pp. 17-25, vol. 924.

Selkoe, Dennis J., "Alzheimer disease: mechanistic understanding predicts novel therapies," Ann. Intern. Med., Apr. 2004, pp. 627-638, vol. 140, No. 8.

Spillantini, Maria Grazia, et al., "Alpha-synuclein in Lewy bodies." Nature, Aug. 1997, pp. 839-840, vol. 388, No. 6645.

Sunderland, Trey, et al., "Decreased beta-amyloid 1-42 and increased tau levels in cerebrospinal fluid of patients with Alzheimer disease," JAMA, Apr. 2003, pp. 2094-20103, vol. 289, No. 16.

Townsend, Matthew, et al., "Effects of Secreted Oligomers of Amyloid {beta}-Protein on Hippocampal Synaptic Plasticity: A Potent Role for Trimers," J. Physiol., Apr. 2006, pp. 477-492, vol. 572, Pt. 2.

Tsai, Julia, et al., "Fibrillar amyloid deposition leads to local synaptic abnormalities and breakage of neuronal branches," Nat. Neurosci., Nov. 2004, pp. 1181-1183, vol. 7, No. 11.

Uversky, Vladimir N., et al., "Evidence for a partially folded intermediate in alpha-synucleinfibrilformation," J. Biol. Chem., Apr. 2001, pp. 10737-10744, vol. 276, No. 14.

Vandermeeren, Marc, et al., "Detection of tau proteins in normal and Alzheimer's disease cerebrospinal fluid with a sensitive sandwich enzyme-linked immunosorbent assay," J. Neurochem., Nov. 1993, pp. 1828-1834, vol. 61, No. 5.

Volles, Michael J., et al., "Vesicle permeabilization by protofibrillar alpha-synuclein: implications for the pathogenesis and treatment of Parkinson's disease," Biochemistry, Jul. 2001, pp. 7812-7819, vol. 40, No. 26.

Volles, Michael J., et al., "Vesicle permeabilization by protofibrillar alphasynuclein is sensitive to Parkinson's disease-linked mutations and occurs by a pore-like mechanism," Biochemistry, Apr. 2002, pp. 4595-4602, vol. 41, No. 14.

Walsh, Dominic M., et al., "Abeta Oligomers- a decade of discovery," J. Neurochem., Jun. 2007, pp. 1172-1184, vol. 101, No. 5.

Walsh, Dominic M., et al., "Deciphering the molecular basis of memory failure in Alzheimer's disease," Neuron, Sep. 2004, pp. 181-193, vol. 44, No. 1.

Walsh, Dominic M., et al., "Amyloid beta-protein fibrillogenesis. Structure and biological activity of protofibrillar intermediates," J. Biol. Chem., Sep. 1999, pp. 25945-25952, vol. 274, No. 36.

Wang, Hai-Wei, et al., "Soluble oligomers of beta amyloid (1-42) inhibit long-term potentiation but not long-term depression in rat dentate gyrus," Brain Res., Jan. 2002, pp. 133-140, vol. 924, No. 2.

* cited by examiner

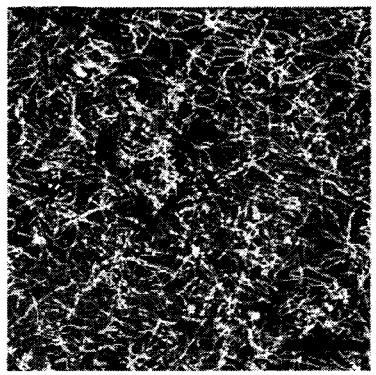
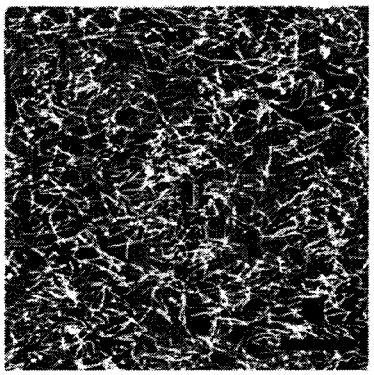
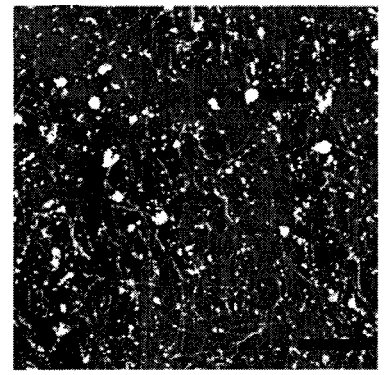
FIG. 2A  FIG. 2B  FIG. 2C
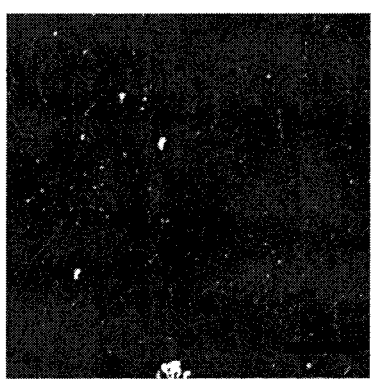
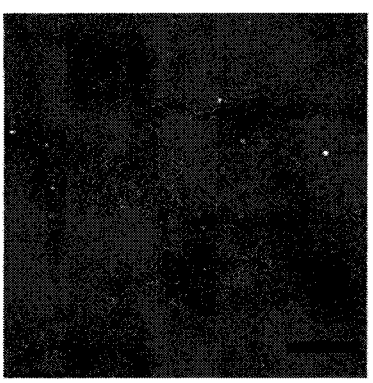
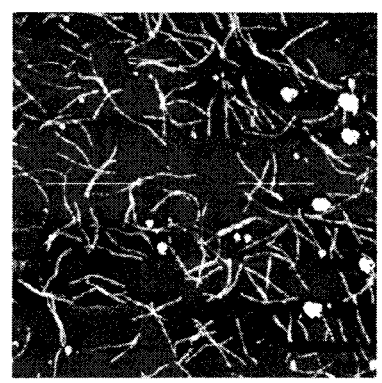
FIG. 2D  FIG. 2E  FIG. 2F

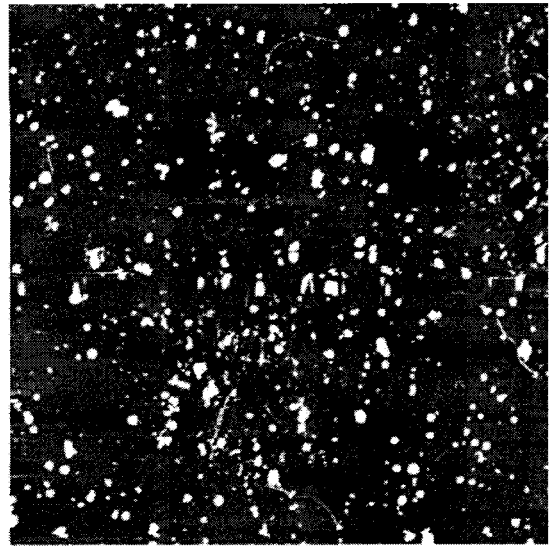
FIG. 3A
FIG. 3B
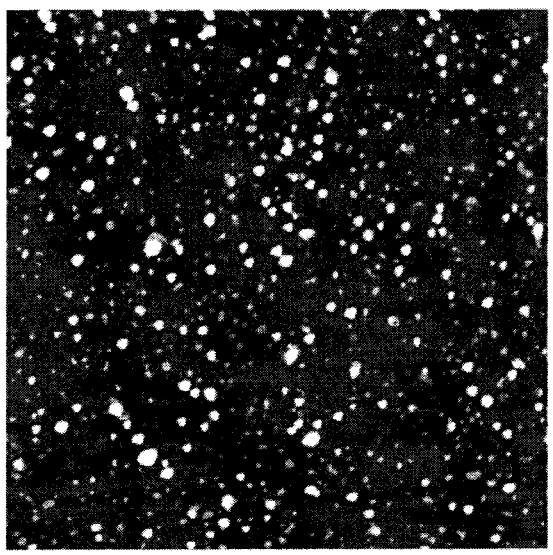
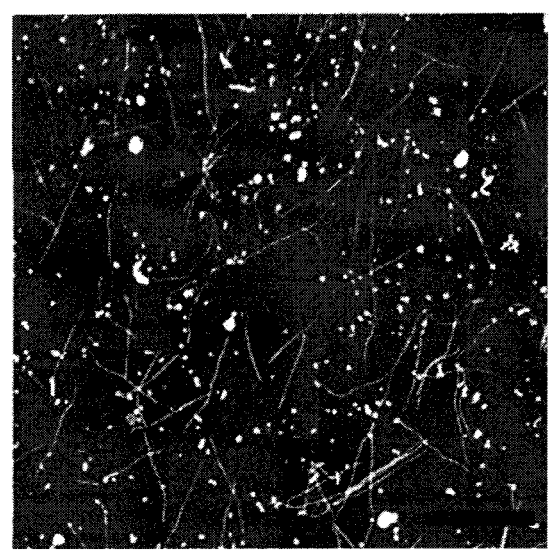
FIG. 3C
FIG. 3D

NATURAL BRAIN DERIVED OLIGOMERS

3D SYNTHETIC Aβ OLIGOMERS

NATURAL BRAIN DERIVED OLIGOMERS

3D SYNTHETIC Aβ OLIGOMERS

SEQUENCE LISTING

<160> NUMBER OF SEQ ID NOS: 2

<210> SEQ ID NO 1
<211> LENGTH: 292
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (2)..(2)
<223> OTHER INFORMATION: Any amino acid

<400> SEQUENCE: 1

```
Glu Xaa Pro Ile Ala Tyr Gly Ser Arg Trp Ile Val Ile Thr Arg Gly
1               5                   10                  15

Pro Ala Gly His Gly Pro Gly Thr Ala Ala Gly Val Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Ser Tyr Gly Ser Val Lys Ile Ser Cys
        115                 120                 125

Phe Asp Tyr Trp Gly Gln Ser Thr Leu Val Thr Val Ser Ser Gly Gly
    130                 135                 140

Gly Gly Ser Gly Gly Gly Gly Ser Gly Gly Gly Gly Ser Glu Ile Val
145                 150                 155                 160

Leu Thr Gln Ser Pro Asp Ser Leu Ala Val Ser Leu Gly Glu Arg Ala
                165                 170                 175

Thr Ile Asn Cys Lys Ser Ser Gln Ser Val Leu Tyr Asn Ser Asn Asn
            180                 185                 190

Lys Asn Tyr Leu Ala Trp Tyr Gln Gln Lys Pro Gly Gln Ser Pro Glu
        195                 200                 205

Leu Leu Ile Tyr Trp Ala Ser Thr Arg Glu Ser Gly Val Pro Asp Arg
    210                 215                 220

Phe Ser Gly Ser Gly Ser Gly Thr Glu Phe Thr Leu Thr Ile Ser Ser
225                 230                 235                 240

Leu Gln Ala Glu Asp Val Ala Val Tyr Tyr Cys Gln Gln Phe Tyr Ser
                245                 250                 255

Thr Pro Pro Thr Phe Gly Gln Gly Thr Lys Leu Glu Ile Lys Arg Ala
            260                 265                 270

Ala Ala His His His His His His Gly Ala Ala Glu Gln Lys Leu Ile
        275                 280                 285

Ser Glu Glu Asp
    290
```

<210> SEQ ID NO 2
<211> LENGTH: 6
<212> TYPE: PRT
<213> ORGANISM: Artificial Sequence

```
<220> FEATURE:
<223> OTHER INFORMATION: Description of Artificial Sequence: Synthetic
      6xHis tag

<400> SEQUENCE: 2

His His His His His His
1               5
```

IMMUNIZATION WITH AMYLOID-BETA OLIGOMERS

RELATED APPLICATIONS

This patent application is a U.S. 371 application of PCT/US2011/057904, which was filed on 26 Oct. 2011, and claims the benefit of priority of U.S. application Ser. No. 61/406,734, filed 26 Oct. 2010; U.S. application Ser. No. 61/406,728, filed 26 Oct. 2010, and U.S. application Ser. No. 61/406,721, filed 26 Oct. 2010, which applications are incorporated by reference herein.

BACKGROUND OF THE INVENTION

Aggregation and deposition of amyloid β-protein ("Aβ" or "beta amyloid") is considered to be a primary pathological event in Alzheimer's disease (AD) (1). While the longer 42-43 amino acid Aβ forms have been implicated in the formation of amyloid plaques (2-4), the aggregation state of the peptide is critical in determining its neurotoxicity. Many different forms of Aβ have been identified and characterized including fibrils, proto-fibrils, annular structures, globular structures, amorphous aggregates and various soluble oligomers (5-9). Numerous studies indicate that small oligomeric morphologies of Aβ are the primary toxic species in AD (10). These small oligomers are also called "low-n oligomers" (i.e., dimers, trimers, or tetramers).

One type of naturally occurring oligomeric Aβ species is a low-n oligomer that is SDS-stable, and inhibits long term potentiation in mammalian hippocampus (13). The naturally occurring low-n SDS-stable Aβ oligomers cause short term memory loss in rats, one of the earliest symptom associated with AD (19), and also affect dendritic morphology in neuronal cells resulting in synaptic losses (20). Concentration levels of this SDS-stable oligomeric form correlate strongly with dementia in AD patients (14). Unlike in vitro generated Aβ, naturally occurring low-n oligomeric aggregate does not dissociate in SDS (e.g., 1-10%) or chaotropic salts (e.g., 1-10%) such as guanidine hydrochloride, and cannot be pelleted from physiological fluids by ultra-centrifugation (15). The naturally occurring low-n oligomeric aggregates can be detected in brain tissue by Western blot analysis (16-17). They are also resistant to the Aβ degrading protease insulin degrading enzyme (IDE) (18).

These low-n SDS-stable oligomers cause short term memory loss in rats, one of the earliest symptom associated with AD (19), and also affect dendritic morphology in neuronal cells resulting in synaptic losses (20). While intracerebral injections of synthetic Aβ oligomers exerted a deleterious effect on learned behavior in rats (21-22), these responses were delayed and the concentrations and amounts of synthetic Aβ were much higher than concentrations of naturally derived SDS-stable low-n Aβ oligomers required to interfere with the memory of a complex learned behavior (19). Together these studies clearly suggest that the naturally derived SDS-stable Aβ oligomers may be important mediators in synaptic dysfunction in early AD and that these naturally derived oligomers behave differently than in vitro derived oligomers.

Passive immunization of various models of Alzheimer's Disease using antibodies against specific forms of conformational epitopes of Aβ structures has been suggested to improve cognitive functions in such models. However, when immunization was attempted with a mixture of Aβ peptide and adjuvant, it was found to produce autoimmune encephalitis. It was speculated that this adverse effect was due to the presence of polysorbate 80 in the final composition. Thus, the idea of immunization against Alzheimer's disease remains compelling but to date no immunization therapy has been effective against this disease.

Accordingly, there exists the need for new therapies and reagents for the treatment of Alzheimer's disease, in particular, therapies and reagents capable of effecting a therapeutic and diagnostic benefit at physiologic (e.g., non-toxic) doses.

SUMMARY OF THE INVENTION

The present invention provides a method of immunizing a subject against Alzheimer's disease comprising administering to said subject a composition comprising an SDS-stable trimeric or tetrameric aggregate of Aβ that is at least partially resistant to denaturation by SDS that is stabilized by a C6 antibody having the sequence of SEQ ID NO:1, wherein the SDS-stable trimeric or tetrameric aggregate of Aβ is optionally conjugated to an exogenous immunogenic carrier or admixed with an adjuvant, or both. In exemplary embodiments, the aggregate of Aβ is a 12-16 kDa oligomeric species of Aβ that is stable in the presence of SDS.

In certain embodiments, the aggregate of Aβ is produced by contacting monomers of Aβ with C6 and producing stabilized aggregates that specifically bind to C6 and are stable to SDS denaturation. In certain embodiments, the Aβ peptide is immunogenic. In some examples, the Aβ peptide is a hapten conjugated to a carrier. In exemplary embodiments, the composition comprises an adjuvant.

In specific embodiments, the subject is immunized with a composition comprising a vehicle and an immunogenic or haptenic fragment of said SDS-stable trimeric or tetrameric aggregate of Aβ that has been conjugated to a carrier. The carrier may be selected from the group consisting of bovine serum albumins, immunoglobulin, thyroglobulin, ovalbumin, tetanus toxoid, keyhole limpet hemocyanin, and lipid moieties.

Another embodiment contemplates a method of preparing an immunogenic Aβ aggregate comprising: monomers of Aβ; contacting said monomers of Aβ aggregates with a composition comprising C6 antibody that has a sequence of SEQ ID NO:1 to form Aβ aggregates; and isolating said Aβ aggregates wherein said method isolates immunogenic Aβ aggregates that comprise an SDS-stable trimeric or tetrameric aggregate of Aβ that is at least partially resistant to denaturation by SDS.

Also contemplated is a composition comprising an SDS-stable trimeric or tetrameric aggregate of Aβ that is at least partially resistant to denaturation by SDS, said composition prepared according to such a method. In specific embodiments, the aggregate of Aβ is conjugated to an exogenous immunogenic carrier or admixed with an adjuvant, or both. In some embodiments, the aggregate of Aβ is a conjugate that further comprises a carrier that is covalently-coupled to said Aβ. For example, the carrier is selected from the group consisting of bovine serum albumin, immunoglobulin, thyroglobulin, ovalbumin, tetanus toxoid, keyhold limpet hemocyanin, and a lipid moiety. In exemplary embodiments, the composition further comprises a pharmaceutically acceptable vehicle and/or adjuvant. As used herein, "SDS-stable" or "at least partially resistant to denaturation by SDS" means that the oligomeric aggregate does not dissociate into the monomer units in SDS (such as in 1% SDS).

The present invention provides a composition comprising trimeric or tetrameric aggregates of Aβ that are at least partially resistant to denaturation by SDS that are operably linked to an antibody fragment that comprises amino acid residues 16-292 of SEQ ID NO:1. In certain embodiments, the antibody fragment comprises amino acid sequence SEQ ID NO:1. In certain embodiments, the antibody fragment is less than 500 amino acids in length, such as between 200-450 amino acids in length, or less than 300 amino acids in length. In certain embodiments, the antibody fragment comprises (consists essentially of, or consists of) amino acid residues 16-292 of SEQ ID NO:1. In specific embodiments, the antibody fragment has an amino acid sequence of SEQ ID NO:1. The antibody fragment is specific for a 12-16 kDa oligomeric species of Aβ.

The present invention provides a method of preparing an immunogenic Aβ aggregate comprising: (a) contacting monomers of Aβ with an antibody fragment to form Aβ aggregates, wherein the antibody fragment is less than 300 amino acids in length and comprises amino acid residues 16-292 of SEQ ID NO:1; and (b) isolating the Aβ aggregates, wherein the Aβ aggregates comprise a trimeric or tetrameric aggregates of Aβ that are at least partially resistant to denaturation by SDS. In certain embodiments, the aggregate of Aβ is produced by contacting monomers of Aβ with C6 and producing stabilized aggregates that specifically bind to C6 and are stable to SDS denaturation.

The present invention further provides a composition comprising an SDS-stable trimeric or tetrameric aggregate of Aβ that is at least partially resistant to denaturation by SDS, wherein the composition is prepared according to the method described above.

In certain embodiments, the aggregate of Aβ in the composition is conjugated to or admixed with, or both, to at least one carrier. In certain embodiments, the Aβ aggregate is covalently-coupled to the carrier. In certain embodiments, the carrier is an immunogenic carrier and/or an adjuvant. In certain embodiments, the immunogenic carrier and/or adjuvant is bovine serum albumin, immunoglobulin, thyroglobulin, ovalbumin, tetanus toxoid, keyhold limpet hemocyanin, or a lipid moiety. In certain embodiments, the composition further comprises a pharmaceutically acceptable vehicle. In certain embodiments, the antibody fragment is immunogenic. In certain embodiments, the aggregate of Aβ is a 12-16 kDa oligomeric species of Aβ that is stable in the presence of SDS.

The present invention provides a method of immunizing a subject against Alzheimer's disease comprising administering to the subject a composition as described above.

BRIEF DESCRIPTION OF THE DRAWINGS

FIGS. 2A-2F. Bio-panning process visualized by AFM. Serial negative panning against A) 1 ng brain derived proteins from which Aβ has been depleted; B) 1 ng brain derived Aβ monomer; and multiple pieces containing 1 μg synthetic Aβ monomers. Panning process was visualized by AFM until no phage binding to synthetic monomers was observed. C) 1st synthetic monomer mica; D) 3rd synthetic monomer mica; E) 5th synthetic monomer mica. F) Recovered phage from last monomer mica was added to mica containing 1 ng dimer sample. Scale bar represents 1 μm.

FIGS. 3A-3D. Phage from 400 clones binds specifically to natural Aβ oligomers. Phage was produced from the 400 clones obtained after the bio-panning process, and added to A) 1 ng Aβ depleted brain sample; B) 1 ng brain derived Aβ monomer; C) 1 μg synthetic Aβ monomer; D) 1 ng brain derived Aβ oligomers. Scale bar represents 1 μm.

DETAILED DESCRIPTION OF THE INVENTION

Figure 1:
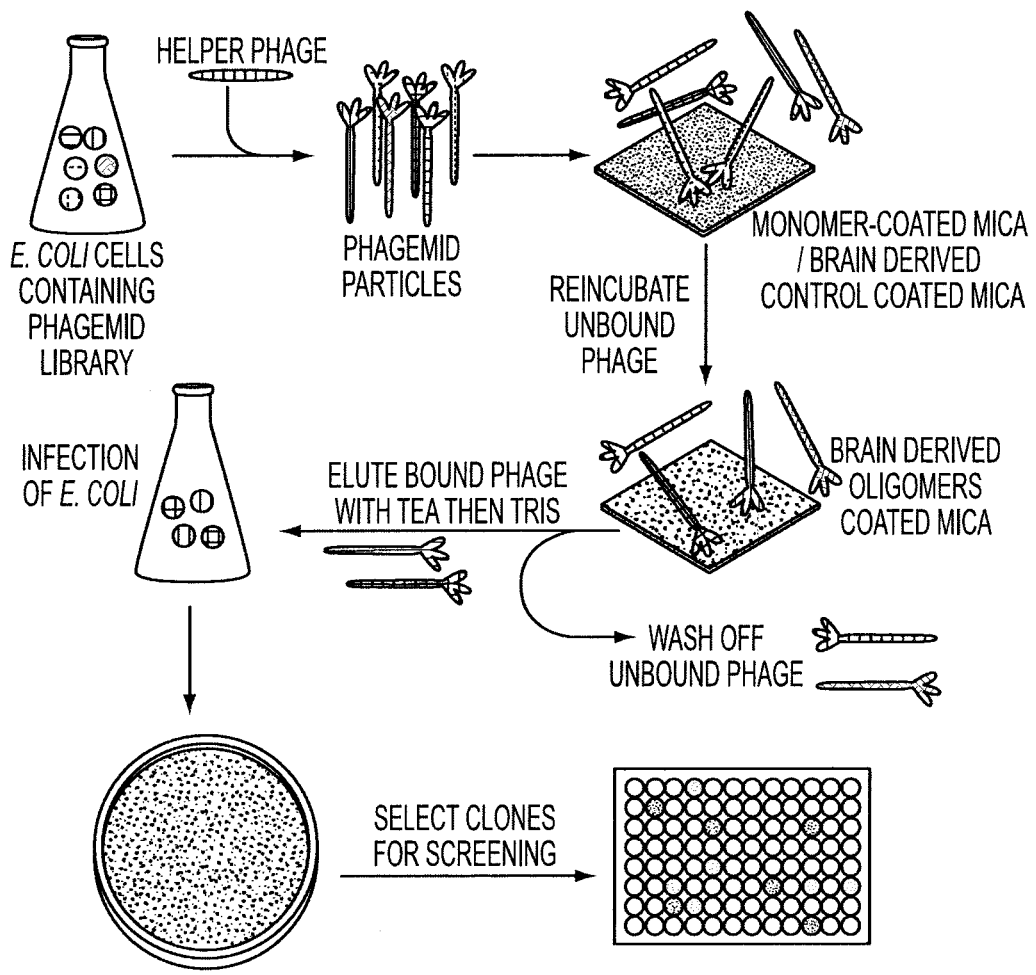
FIG. 1. Bio-panning against natural Aβ oligomers—Schematic. Panning protocol showing different steps involved in isolating scFv against low concentrations of natural brain derived Aβ oligomers.

Soluble cell-derived oligomers of Aβ have been shown to play a critical role in disrupting synaptic plasticity and behavior in Alzheimer's Disease (AD) and developing reagents against these species represents a potential therapeutic option. In the present invention, using a novel bio-panning protocol to identify single chain antibody fragments (scFv, also called nanobodies) against low (pico-molar) quantities of cell-derived Aβ dimers, the inventors identified a binding reagent with therapeutic and diagnostic properties. The method involved performing negative panning against non-desired antigens such as brain derived proteins, Aβ monomers or fibrillar Aβ. The negative panning steps were visualized by atomic force microscopy (AFM) and were continued until no more phage binding to the monomers was observed. Subsequently, positive panning was performed by adding the phage in the supernatants from the negative panning to naturally occurring low-n SDS-stable Aβ oligomers. This positive panning step resulted in isolation of phage that bound specifically to the naturally occurring low-n SDS-stable Aβ oligomers but not to monomeric Aβ, fibrillar Aβ or other cell derived proteins. Phage eluted from the oligomer mica was screened against dilutions of antigen concentrations to isolate phage having highest affinities. Clone C6 was isolated which had high expression levels, and bound specifically to brain derived low-n SDS-stable Aβ oligomers. The C6 nanobodies also recognized a 12-16 kDa Aβ fragment in cell media extracted from a human amyloid precursor over-expressing cell line, and protected the cells from intrinsic toxicity. The C6 nanobodies prevented aggregation of synthetic Aβ in vitro and stabilized the formation of toxic low-n SDS-stable Aβ oligomers. The C6 nanobodies could specifically detect Aβ aggregates in brain tissue from AD patients and also in younger transgenic mouse models of AD. Since this C6 nanobody recognized a small soluble oligomeric morphology of Aβ generated in vivo, it has potential as a diagnostic for the early detection of AD.

The inventors developed a bio-panning technique that combined phage display technology and atomic force microscopy (AFM) that enabled the inventors to isolate antibody fragments (also called nanobodies) against specific protein morphologies. Using this technology, the inventors isolated nanobodies specific for two different oligomeric morphologies of synthetic Aβ. Both of the nanobodies inhibited Aβ aggregation and toxicity towards neuronal cells, and both recognized Aβ aggregates in human AD brain tissue (25-28). Here the inventors report a modified bio-panning protocol that enables the isolation of nanobodies that specifically recognize the brain-derived SDS-stable Aβ oligomers implicated in LTP dysfunction and impairment of synaptic plasticity without also recognizing monomeric, fibrillar or synthetic oligomeric Aβ. By incorporating a series of "negative panning" steps, the inventors eliminated essentially 100% of phage binding to off-target antigens (including Aβ monomers and other brain derived proteins) and were able to isolate nanobodies to brain derived Aβ oligomers using only picograms of an enriched sample using a single round of bio-panning. Using this process the clone C6 was selected because it had suitable specificity and high expression levels.

The C6 nanobody specifically binds brain derived Aβ aggregates but not synthetic Aβ aggregates. Cell media from a cell line that overexpresses human amyloid precursor protein (hAPP) probed with C6 nanobodies showed a band corresponding to 16 kDa, suggesting that the C6 nanobody recognizes a tetrameric form of Aβ. C6 also recognized natural Aβ in the brain tissue from mouse models of AD, and natural Aβ in the brain tissue from human AD patients. C6 nanobodies prevented aggregation of synthetic Aβ monomers into fibrils and stabilized the formation of SDS-stable low-n oligomers that were toxic to SH-SY5Y neuroblastoma cells in vitro.

In certain embodiments, the C6 nanobody has a sequence of SEQ ID NO:1:

EXPIAYGSRWIVITRGPAGHGPGTAAGVGGGLVQPGGSLRLSCAA

SGFTFSSYAMSWVRQAPGKGLEWVSAISGSGGSTYYADSVKGRFTISRDN

SKNTLYLQMNSLRAEDTAVYYCAKSYGSVKISCFDYWGQSTLVTVSSGGG

GSGGGGSGGGGSEIVLTQSPDSLAVSLGERATINCKSSQSVLYNSNNKNY

LAWYQQKPGQSPELLIYWASTRESGVPDRFSGSGSGTEFTLTISSLQAED

VAVYYCQQFYSTPPTFGQGTKLEIKRAAAHHHHHHGAAEQKLISEED

In certain embodiments, the C6 nanobody lacks from 1 to 15 of the initial amino acids of SEQ ID NO:1.

Thus, in a broad sense the C6 composition of the present invention may be described as a compound that is an Aβ binding compound. This compound is used in the present invention to produce SDS-stable trimeric or tetrameric aggregates of Aβ. This aggregate population is isolated using standard peptide isolation and purification techniques to produce a substantially purified composition comprising SDS-stable trimeric or tetrameric aggregates of Aβ. This composition is then used in the treatment or prophylaxis of neurodegenerative disorders in which amyloid plaques accumulate.

The methods of the present invention are conducted to provide early stage prevention of Alzheimer's Disease. As explained herein the C6 nanobody of the invention is one that specifically recognizes the brain-derived SDS-stable Aβ oligomers and produces a stabilized form of trimeric or tetrameric aggregates of Aβ. This form of Aβ oligomers is identified in a biological sample taken from a subject having AD or indeed any brain derived oligomers of as a synthetic composition and stabilized by contacting heterogeneous mixtures of Aβ with the C6 composition. The highly stabilized and toxic forms of Aβ oligomers in the sample are then isolated into a purified composition and administered in a vaccination protocol to a patient that has or is likely to develop Alzheimer's Disease.

Thus, the present invention relates to methods for combating cell degeneration or dysfunction resulting from amyloidogenic conditions. More specifically, the invention especially relates to the use, in the preparation of a medicament for the treatment of neurodegenerative disease that is characterized by accumulation of SDS-stable trimeric or tetrameric aggregates of Aβ, of an immunogenic compound which is capable of inducing an immune response against such aggregates of Aβ, or an effective amount of a hapten of such aggregates combined with appropriate carriers and/or adjuvants to render the resulting combination capable of inducing an immune response against a toxic forms of Aβ aggregates.

The inventors have now found that it is possible to reduce amyloid plaque formation occurring in a neurodegenerative disease such a Alzheimer's Disease, by administering an immunogenic derivative of a stabilized form of SDS-stable trimeric or tetrameric aggregates of Aβ, enabling the production of antibodies directed against toxic oligomers of Aβ.

The invention thus concerns the use of a composition capable of producing an immune response against aggregates of Aβ in the preparation of a medicament for vaccination of an animal against amyloid plaque formation thereby inhibiting amyloid plaque formation caused by deposition of toxic forms of Aβ in an animal, especially in a mammal and more particularly in human. It should be understood that the term "mammal" refers to animals of the mammal class of animals including human.

According to the present invention, a composition is considered to in vivo inhibit the development of a neurodegenerative disease such as Alzheimer's Disease if administration of the composition to a mammal of an effective amount of the composition can significantly reduce the formation of Aβ plaques in vivo. A reduction is considered significant if the reduction of Aβ plaques is at least about 10%, at least about 50%, at least about 80% or at least about 90%. Plaque formation may be determined by any method generally used in the diagnosis or determination of Alzheimer's disease plaques.

In one embodiment, the in vivo inhibition of plaque formation can be achieved by the administration of a composition comprising an effective amount of an immunogenic composition capable of inducing an immune response against a stabilized form of SDS-stable trimeric or tetrameric aggregates of Aβ. The inventors have shown that such a stabilized Aβ aggregate can be isolated from brain derived Aβ aggregates with a C6 antibody and isolating those aggregates that specifically bind to C6.

Accordingly, the isolated stabilized Aβ aggregate can be used to produce a therapeutic outcome by the administration of a composition comprising an effective amount of such an aggregate to a subject that has or is suspected of developing Alzheimer's Disease in an amount effective for said subject to produce an antibody response to the composition.

The invention therefore relates to an immunogenic composition that comprises an effective amount of an immunogenic compound which is capable of inducing an immune response against a specific form of SDS-stable trimeric or tetrameric aggregates of Aβ, or an effective amount of such an SDS-stable trimeric or tetrameric aggregates of Aβ acting as an hapten combined with appropriate carriers and/or adjuvants to render the resulting combination capable of inducing an immune response against amyloid plaque formation.

The inventors have identified a C6 reagent ("C6 nanobody") specifically recognizes the toxic brain derived oligomeric Aβ aggregates. When incubated with monomeric Aβ, the C6 nanobody catalyzes formation of SDS stable toxic oligomeric Aβ aggregates similar to those isolated from brain tissue. Since the C6 nanobody catalyzes formation of these toxic aggregates in vitro, it is easy to generate large amounts of pure oligomeric Aβ similar to the brain derived material. These aggregated species will be useful for active immunization studies since they generate antibodies specifically against toxic Aβ species and not against other Aβ forms. The amino-terminal region of Aβ is highly immunogenic and in all aggregated forms of Aβ, the amino terminal is exposed. Therefore oligomeric aggregates of Aβ generated in the presence of the C6 nanobody similar to all aggregated Aβ forms, have highly antigenic amino terminals exposed on the surface. Immunization with these aggregates result in generation of antibodies to the amino terminal of Aβ. These antibodies recognize all forms of Aβ including monomeric and fibrillar. In order generate antibodies that specifically recognize the oligomeric Aβ species, the inventors incubate N-terminal deletions of Aβ with C6 to generate the respective oligomeric species, but without the amino-terminal epitope. Immunization with these species generates an immune response specific for the toxic naturally occurring cell derived species recognized by the C6 nanobody.

The immunization protocols proposed here are much more specific than those previously utilized and should minimize the risk of inflammatory responses in the brain since they target very specific oligomeric structures which are present only in very small concentrations. Conventional approaches target monomeric or fibrillar Aβ forms which are present in much higher concentrations and do not represent the toxic species that need to be targeted.

The immunogenic composition can be used for the preparation of a medicament for inhibiting the development or progression of neurodegenerative disease in an animal, as here above defined, and especially for the preparation of a vaccine medicament for the treatment of neurodegenerative disease associated with Aβ plaque formation as exemplified by Alzheimer's disease.

As used herein the term "immune response against Aβ plaque formation/SDS-stable trimeric or tetrameric aggregates of Aβ," means that the humoral immune response is sufficient to form antibodies that bind to one or more endogenous forms of Aβ, thus neutralizing their ability to form toxic amyloid plaques, in neuronal or glial cells or in the brain of an animal. In a specific embodiment, the "immune response" is directed against a specific SDS-stable form of Aβ that is resistant to denaturation by SDS but is not directed against Aβ that but does not bind monomeric, fibrillar or other oligomeric forms of Aβ that are generated in vitro. In specific embodiments, the immunogenic compound or hapten comprises or essentially consists of a SDS-stable form of Aβ that is resistant to denaturation by SDS which if it does not produce an immune response separately can be rendered immunogenic when combined with appropriate carriers and/or adjuvants.

In a certain embodiment of the invention, said immunogenic compound or hapten comprises or essentially consists of an SDS-stable Aβ aggregate that is resistant to denaturation by SDS characterized by a molecular weight of 12-16 kDa.

The SDS-stable Aβ aggregate that is resistant to denaturation by SDS may be fused to other heterologous polypeptidic sequences. For example such aggregates can be coupled to one single or a few heterologous epitopes to specifically promote humoral immunological responses.

When an SDS-stable Aβ aggregate that is resistant to denaturation by SDS that is contained in the immunogenic composition of the invention is not immunogenic per se, but is a hapten, it can be made immunogenic by coupling the hapten to a carrier molecule such as bovine serum albumin (BSA). Other carriers include immunoglobulin molecules, thyroglobulin, ovalbumin, tetanus toxoid, keyhole limpet hemocyanin or lipid moieties. Various carrier molecules and methods for coupling a hapten to a carrier molecule are well-known in the art (Bioconjugation. Protein coupling techniques for the biomedical sciences". 364-482, Ed. Aslam M. & Dent A. Mcmillan Reference LTD, UK, 1998).

The immunogenic composition of the invention is formulated for administration to an animal or a patient suffering from a disease caused by amyloid plaque formation, and especially to an animal or a patient suffering of neurodegenerative disease such as Alzheimer's Disease.

The immunogenic composition of the invention can be administered alone or in combination with an acceptable vehicle, including water, saline, glycerol, ethanol, etc. The compositions can also be administered in combination with other therapeutic agents, especially useful for the treatment of amyloid plaque formation, and/or useful for the treatment of neurodegenerative diseases such as Alzheimer's Disease. Any therapeutic agent typically used for the treatment of Alzheimer's disease may be used in combination with an immunization therapy as described herein to achieve an amelioration of one or more of the symptoms or characteristics of the disease. Various drugs for the treatment of AD are currently available as well as under study and regulatory consideration. The drugs generally fit into the broad categories of cholinesterase inhibitors, muscarinic agonists, anti-oxidants or anti-inflammatories. Galantamine (Reminyl), tacrine (Cognex), selegiline, physostigmine, revistigmin, donepezil, (Aricept), rivastigmine (Exelon), metrifonate, milameline, xanomeline, saeluzole, acetyl-L-carnitine, idebenone, ENA-713, memric, quetiapine, neurestrol and neuromidal are just some of the drugs proposed as therapeutic agents for AD that can be used in combination therapy in the present invention for the therapeutic intervention of AD. Typically, the compositions are prepared as an injectable composition, either as a liquid solution or a suspension. However, solid compositions suitable for solution or suspension in liquid vehicles prior to injection can also be prepared.

An effective amount of the immunogenic compound or hapten, useful for inducing an immune response against proapoptotic neurotrophin can be determined on a case-by-case basis. According to a certain embodiment, the immunogenic composition is effective to produce an immune response that is characterized by a serum titer of at least 1:1000 with respect to the antigenic determinant against which the immune response is directed. In yet another embodiment, the serum titer is at least 1:5000 with respect to the neurotrophin component. According to a specific embodiment, the immune response induced by the immunogenic composition is characterized by a serum amount of immunoreactivity corresponding to more than four times higher than a serum level of immunoreactivity measured in a pretreatment control serum sample. This latter characterization is particularly appropriate when serum immunoreactivity is measured by ELISA techniques, although it can apply to any relative or absolute measurement of serum immunoreactivity.

For example, an effective amount of the active ingredient containing the SDS-stable aggregate is comprised between 0.5 µg and 2000 µg of the immunogenic aggregate.

In certain embodiments, the immunogenic composition is formulated as a vaccine. In certain embodiments, the vaccine composition includes generally specific excipients and/or adjuvants, to enhance the immune response.

For example, an adjuvant can be a particulate or non-particulate adjuvant. A particulate adjuvant usually includes, without limitation, aluminium salts, calcium salts, water-in-oil emulsions, oil-in-water emulsion, immune stimulating complexes (ISCOMS) and ISCOM matrices (U.S. Pat. No. 5,679,354), liposomes, nano- or micro-particles, proteosomes, virosomes, stearyl tyrosine, and gamma-inulin. A non-particulate adjuvant usually includes, without limitation, muramyl dipeptide (MDP) and derivatives, e.g., treonyl MDP or murametide, saponins, e.g., Quil A and QS21, lipid A or its derivative 4' monophosphoryl lipid A (MPL), various cytokines including gamma-interferon and interleukins 2 or 4, carbohydrate polymers, diethylaminoethyl dextran and bacterial toxins, such as cholera toxin. Adjuvants formulation designed to maximize specific immune response can also be used. Such adjuvants include those known to those of skill in the art, for example, adjuvants may include one or more from the group consisting of aluminium hydroxide, aluminium phosphate, MPL1M, QS-21 or incomplete Freund's adjuvant. According to a specific embodiment, such immunogenic compositions may include a plurality of immunogenic compounds effective to induce an immune response in a subject.

The invention also relates to the method for treating or preventing neuronal or glial cell amyloid plaque deposition and/or formation or development of neurodegenerative disease, comprising the administration to an animal or a patient suffering from or suspected of developing a neurodegenerative disease of a composition comprising an SDS-stable Aβ aggregate that is resistant to denaturation by SDS that is prepared/isolated as described herein. More specifically, the invention relates to a method for treating or preventing Alzheimer's disease in a subject comprising the administration to an animal or a patient of an immunogenic composition capable of inducing an immune response directed against the SDS-stable Aβ aggregates that is resistant to denaturation by SDS.

Immunization regimens that may be used in achieving an immune response against toxic, SDS-stable Aβ aggregates may include administration of the immunogenic composition, in multiple dosages, for example over a 6 month period for an initial immunization followed by booster injections at periodic intervals, for example 6 weeks period, or according to patient need, as assessed by measuring immunological response.

The compositions of the invention as described above can be administered according to any pharmaceutically effective route, including for example, peritoneal, oral, intranasal, subcutaneous, intramuscular, topical or intravenous administration.

The active ingredients of the compositions including the immunogenic or hapten compounds can be prepared as pharmaceutical composition for administration to a subject. Such compositions will ideally be formulated into a pharmaceutically acceptable carrier. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

The therapeutic immunization using the specific SDS-stable Aβ aggregates according to the present invention may advantageously be combined with a method of diagnosing and monitoring the efficacy of the therapeutic intervention. Such diagnostic methods may use any antibody that detects plaque formation. One such antibody is the C6 nanobody used to isolate the immunogenic compositions of the present invention. A variety of immunodetection methods are available. Such immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature.

In general, the immunobinding methods include obtaining a sample suspected of containing a protein, polypeptide and/or peptide (in this case an amyloid plaque), and contacting the sample with a first antibody, monoclonal or polyclonal, as the case may be, under conditions effective to allow the formation of immunocomplexes.

The immunobinding methods include methods for detecting and quantifying the amount of amyloid plaques component in a sample and the detection and quantification of any immune complexes formed during the binding process. Here, one would obtain the test and contact the sample with an antibody that will detect the plaque components and then detect and quantify the amount of immune complexes formed under the specific conditions. Performing such a detection step before and after administration of a therapy or during the course of Alzheimer's disease treated with an immunogenic composition of the invention allows an assessment of the efficacy of the treatment.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibody molecules specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

As noted above, the antibody specific for the plaque itself be linked to a detectable label, wherein one would then simply detect this label, thereby allowing the amount of the primary immune complexes in the composition to be determined. Alternatively, the first antibody that becomes bound within the primary immune complexes with the plaque may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for antibody that is used to detect the plaque is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody specific for the disorder being detected is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays, in their most simple and/or direct sense, are binding assays. Certain immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, antibodies that are specific for the disease to be detected are immobilized onto a selected surface exhibiting protein affinity, such as a well in a polystyrene microtiter plate. Then, a test composition suspected of containing the diseased cells, such as a clinical sample (e.g., a biological sample obtained from the subject), is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with antibodies. After binding and/or washing to remove non-specifically bound immune complexes, the bound anti-antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes.

In coating a plate with either biological sample to be tested or the diagnostic antibody used to perform the testing, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions in certain embodiments include diluting the biological sample to be tested and/the diagnostic antibody composition with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures, in certain embodiments, on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzothiazoline-6-sulfonic acid (ABTS), or $H_2O_2$, in the case of peroxidase as the enzyme label. Quantification is then achieved by measuring the degree of color generated, e.g., using a visible spectra spectrophotometer.

In various aspects of the invention, it will be desirable to further subject patients to more traditional AD diagnostic approaches. Such general approaches for diagnosis are set out below.

The diagnosis of both early (mild) cognitive impairment and AD are based primarily on clinical judgment. However, a variety of neuropsychological tests aid the clinician in reaching a diagnosis. Early detection of only memory deficits may be helpful in suggesting early signs of AD, since other dementias may present with memory deficits and other signs. Cognitive performance tests that assess early global cognitive dysfunction are useful, as well as measures of working memory, episodic memory, semantic memory, perceptual speed and visuospatial ability. These tests can be administered clinically, alone or in combination. Examples of cognitive tests according to cognitive domain are shown as examples, and include "Digits Backward" and "Symbol Digit" (Attention), "Word List Recall" and "Word List Recognition" (Memory), "Boston Naming" and "Category Fluency" (Language), "MMSE 1-10" (Orientation), and "Line Orientation" (Visuospatial). Thus, neuropsychological tests and education-adjusted ratings are assessed in combination with data on effort, education, occupation, and motor and sensory deficits. Since there are no consensus criteria to clinically diagnose mild cognitive impairment, various combinations of the above plus the clinical examination by an experienced neuropsychologist or neurologist are important to proper diagnosis. As the disease becomes more manifest (i.e., becomes a dementia rather than mild cognitive impairment), the clinician may use the criteria for dementia and AD set out by the joint working group of the National Institute of Neurologic and Communicative Disorders and Stroke/AD and Related Disorders Association (NINCDS/ADRDA). On occasion, a clinician may request a head computed tomography (CT) or a head magnetic resonance imaging (MRI) to assess degree of lobar atrophy, although this is not a requirement for the clinical diagnosis.

Vaccines of the Invention

The present invention provides a vaccine for use to protect mammals against the AD. In one embodiment of this invention, the composition can be delivered to a mammal in a pharmacologically acceptable vehicle. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest. Vaccines of the present invention can also include effective amounts of immunological adjuvants, known to enhance an immune response.

To immunize a subject, the composition is administered parenterally, usually by intramuscular or subcutaneous injection in an appropriate vehicle. Other modes of administration, however, such as oral, intranasal or intradermal delivery, are also acceptable.

Vaccine formulations will contain an effective amount of the active ingredient in a vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies. Effective dosages can be readily established by one of ordinary skill in the art through routine trials establishing dose response curves. The subject is immunized by administration of the composition in one or more doses. Multiple doses may be administered as is required to maintain a state of therapeutic effect.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the composition can be isolated, lyophilized and stabilized, as described above. The composition may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," *Sem. Hematol.*, 30:3-15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

Formulations and Methods of Administration

The compositions of the invention may be formulated as pharmaceutical compositions and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In certain cases, one may include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, in certain embodiments, the methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, or from about 0.5-10 wt-%. The concentration in a semi-solid or solid composition such as a gel or a powder will be about 0.1-5 wt-%, or about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, in the range of 6 to 90 mg/kg/day, or in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, about 1 to 50 μM, or about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

EXAMPLES

Materials and Methods

Phage Display scFv Library.

The Sheets phage display scFv library comprising over $10^{12}$ different scFv fragments was provided by Dr Yu (Eunice) Zhou, Department of Anesthesia, University of San Francisco (29).

Phage Production.

Production of phage from the Sheets library was performed essentially as described (30). Briefly, E. coli TG1 cultures in the exponential phase were infected with helper phage VCSM13 (Strategene) at a ratio of 1:50 (number of bacterial cells/phage particles) for 30 minutes at 37° C. without shaking. Cultures were grown for 1-2 hr at 37° C. in the presence of 100 μg/mL ampicillin and 25 μg/mL kanamycin for phage production followed by centrifugation at 3000×g for 20 minutes. The pellet was removed and resuspended in 1 L 2×YT with 100 μg/mL ampicillin and 25 kanamycin, and grown overnight at 30° C. Phage were purified from the supernatant by polyethylene glycol (PEG) and NaCl precipitation and resuspended in PBS (phosphate-buffered saline) and used for panning.

Brain Derived Antigens.

The brain derived antigens were a generous gift from Dr Dennis Selkoe (Harvard Medical School, Boston). A 40 ng aliquot of enriched brain derived samples containing SDS-stable Aβ oligomers or Aβ monomers were obtained as lyophilized powder. Prior to the bio-panning experiments, the samples were re-suspended in TBS buffer to a final Aβ concentration of 5 nM, aliquoted, and stored at −20° C. Brain samples from which Aβ has been completely depleted by immunoprecipitation were used as a control.

Preparation of Synthetic Aβ.

Aβ40 was synthesized in the Proteomics and Protein Chemistry Laboratory at Arizona State University, purified by HPLC, lyophilized and stored as its Trifluoroacetate salt Aβ40 at −20° C. Samples were prepared as previously described (28). Briefly, Aβ40 was solubilized in 1,1,1,3,3,3-hexafluoro-2-propanol (HFIP) at a concentration of 1 mg/mL to avoid aggregates. Aliquots of 250 μL were air dried and stored at −20° C. Prior to use, the aliquots of monomeric Aβ were re-suspended in dimethyl-sulfoxide (DMSO) and diluted to final concentration in Tris-HCl buffer (20 mM Tris, 150 mM NaCl, pH 7.5).

Atomic Force Microscope (AFM) Imaging.

AFM analysis was performed as described previously (31). Samples were deposited on mica, dried and imaged in air using a MultiMode AFM NanoScope IIIA system (Veeco/Digital Instruments, Santa Barbara, Calif.) operating in tapping mode using silicon probes (Model: OTESPA, Veeco, Santa Barbara, Calif.) (31).

Bio-Panning Against Natural Brain Derived Antigen.

The bio-panning process was performed in 2 steps. The first step, referred to as "Negative panning" was used to eliminate phage that bind to non-desired antigen. The second step, "Positive panning" was used to isolate phage that bind the target antigen (FIG. 1).

1. Negative Panning.

Negative panning was performed to eliminate phage binding to non-desired antigens. A 1 ng aliquot of brain derived control proteins, 1 ng of brain derived monomers and 1 μg of synthetic monomers were deposited on multiple pieces of mica and air dried. A 100 μL aliquot of amplified phage containing $10^{12}$ phage units was serially added first to the brain derived control, next to brain derived monomers, and finally to multiple pieces of synthetic monomers in 25 µl aliquots. The phage was allowed to incubate with each piece of antigen coated mica for 10 min before removal and addition to the next sample. The negative panning steps were performed in duplicate with one set used for panning and the second set used for AFM imaging to monitor the panning process. Serial addition of phage to mica substrates containing the synthetic Aβ monomer samples was continued until no phage was observed binding to antigen by AFM analysis. Aliquots of 1×PBS were periodically added to restore phage solution volume lost due to evaporation from mica surface.

2. Positive Panning.

A 1 ng aliquot of natural brain derived SDS-stable Aβ oligomers was deposited onto mica and air dried. After all the non-binding and non-specific binding phage were eliminated in the negative panning steps, a 20 µL aliquot of remaining phage was added to mica surface, incubated for 10 min and then sequentially washed with 2 mL PBS-0.1% Tween-20, 2 mL PBS and 2 mL water and then air dried. This positive panning step was performed in duplicate, with one set used for the panning steps and the second set used for AFM imaging to monitor the panning process. Bound phage particles were eluted and recovered as previously described (25, 27).

Selection of High Affinity Clones.

Approximately 400 clones were recovered from the positive panning step and each was individually grown in 96 well plates. Phage production from the individual clones was induced by addition of helper phage as previously described. Serial dilutions of the natural brain derived Aβ oligomers (1/10-1/10,000) were deposited on mica. Phage from all 400 clones were pooled and added to each of the mica samples. Unbound phage were washed off with 2 mL PBS-0.1% Tween-20 and water and remaining phage was visualized by AFM. Phage was eluted from each of the dilutions as described above and used to infect E. coli TG1 and plated onto LB agar plates. Single clones were picked from the lowest dilution plate, plasmid DNA was isolated and checked by sequence analysis to verify sequence of the isolated nanobodies.

Dot Blot Assay to Screen for Expression Levels.

To check expression levels, plasmid DNA from the positive clones identified above were transformed into the non-suppressor E. coli HB2151 for production of soluble nanobody. Individually selected clones were grown and nanobody production was induced by addition of 1 mM isopropyl-β-D-thiogalactopyranoside (IPTG) as described earlier (30). A 5 µl aliquot of the supernatant and lysate fractions from the different clones were deposited onto a gridded nitrocellulose membrane. The membrane was blocked with 5% Milk-PBS (5 g Carnation nonfat dry milk in 100 ml PBS buffer) for at least one hour at room temperature followed by incubation overnight with a 1:1000 dilution of the primary anti-myc tag antibody 9E10 (Sigma). Immunoreactivity was detected after a 1-h incubation using a 1:1000 dilution of the secondary anti-mouse IgG HRP antibody (Sigma). The membrane was stained with 3.3'-Diaminobenzidine Tetrahydrochloride (DAB) solution (Sigma). One phage clone, which encoded scFv C6 (also called "nanobody C6") was selected for further experiments based on its higher expression levels.

Binding Specificity by Phage Assay.

To confirm binding specificity of C6 nanobody to brain derived oligomers, phage encoding the C6 nanobody, as well as phage encoding a nanobody specific for a synthetic oligomeric morphology of Aβ, A4, were produced from E. coli TG-1 essentially as described (25, 27). Purified phage were added to naturally-derived or synthetically-derived Aβ oligomers on the mica surface, and phage binding to the antigen was visualized by AFM.

Production and Purification of Soluble Nanobody.

To express and purify soluble nanobody, nucleic acid encoding C6 nanobody was first cloned into a pIT2 E. coli expression vector, and transformed into E. coli Hb2151. The supernatant and cell lysate from a 1 L culture were combined and concentrated in a tangential flow filter (Millipore) using a 10 kDa filter membrane (Millipore). The concentrated supernatant/lysate was used for dot blot and western blot assays.

For nanobody purification, a 6×His tagged nanobody was purified by mixing with 1 ml Nickel NTA sepharose beads (Qiagen, CA) for 2 hours, followed by elution with an imidazole gradient. Fractions containing nanobodies were pooled and dialyzed into 1×PBS. Protein expression and purity was checked with SDS-PAGE and western blotting. A bicinchonic acid (BCA) protein assay (Sigma) was used to determine nanobody concentration as previously described (28).

Culture of Human APP Over-Expressing Cells.

The C6 nanobody was tested for its ability to recognize naturally derived Aβ oligomers secreted by a Chinese hamster ovary (CHO) cell line stably transfected with cDNA encoding mutant human APP751 (7PA2). The 7PA2 cells were a kind gift from Dr. Dennis Selkoe (Harvard Medical School, Boston). Cells were grown in Dulbecco Modified Eagle medium (DMEM) containing 10% fetal bovine serum, 1% L-glutamine and 1% penicillin/streptomycin (Gibco). Selection for mutant APP expressing cells was performed using 1 mg/ml G-418 (Calbiochem), an amyloglycoside antibiotic. Once the cells reach 95% confluence, 7PA2 cells were plated onto 6 well plates and used for further studies.

Detection of Aβ Expressed by Human APP Over-Expressing Cells.

The 7PA2 cells were grown for 2 days after which the cell culture media was removed and concentrated. Total protein concentration was determined by BCA and 25 µg of cell culture media was separated on a 10% Tris/Tricine gel and transferred onto a 0.2 µm nitro-cellulose membrane (Bio-Rad). The membrane was probed for 24 hours with the concentrated supernatant/lysate containing C6 nanobody. The membrane was then incubated overnight with a 1/1000 dilution of primary anti-myc tag antibody. Immunoreactivity was detected following a 1-hour incubation with a 1/1000 dilution of a HRP conjugated goat anti-mouse IgG as secondary antibody. The membrane was stained with DAB solution as described above (Sigma).

Aβ Aggregation Assay.

Aggregation of monomeric Aβ, prepared as described above, was initiated by dilution in Tris-HCl buffer to a concentration of 50 µM and incubation in a 37° C. incubator. For co-incubation studies of Aβ with C6 nanobody, a 50 µM solution of monomeric Aβ was incubated with 5 µM C6 at 37° C. Aliquots were removed at selected time intervals for further analysis.

Thioflavin T (ThT) Fluorescence Assay.

ThT fluorescence assay was performed essentially as described (42). Fluorescence intensity was monitored at an excitation wavelength of 450 nm and an emission wavelength of 482 nm with a Shimadzu PF-3501PC spectrofluorophotometer (Shimadzu, Japan) using 1 cm light-path quartz cuvettes with both excitation and emission bandwidths of 5 nm (27-28, 32). All ThT fluorescence experiments were performed in triplicate. The standard errors were analyzed with Excel.

Tris-Tricine SDS-PAGE and Western-Blot.

Western blot analysis was used to characterize the Aβ species generated upon co-incubation with C6 nanobody. Aliquots of the Aβ sample incubated with or without C6 nanobody corresponding to different time points of aggregation were removed and separated on a 10% Tris/Tricine gel and transferred onto a 0.2 μm nitro-cellulose membrane (Bio-Rad). The membrane was probed for 24 hours with a 1/1000 dilution mouse monoclonal antibody 6E10 (Calbiochem, USA) which recognizes the N-terminus of the Aβ peptide and immunoreactivity was detected following a 1-hour incubation with a 1/1000 dilution of a HRP conjugated goat anti-mouse IgG as secondary antibody to determine monomeric and oligomeric Aβ levels in the aggregated samples.

SH-SY5Y Neuroblastoma Cell Toxicity Assay.

The human neuroblastoma cell line SH-SY5Y was obtained from the American Tissue Culture Collection (USA). Cells were cultured as previously described (27-28). To test for toxicity, a 5 μL aliquot of the Aβ samples corresponding to different time points of aggregation with or without C6 nanobody was added to the cells and incubated for 48 hours. Cytotoxicity was measured by Lactose dehydrogenase (LDH) release assay (Sigma) as described (26-28, 32). Three wells were used for each sample, and each experiment was performed in triplicate. The data are reported as the percentage of LDH released compared to the LDH released from wells with Tris-HCl buffer alone (26, 32-33). The standard errors were analyzed with Excel.

Brain Dot Blot Assays.

Mouse brain tissue from wild type and triple transgenic (3×Tg) mice were generously provided by Dr John Valla (Barrow Neurological Institute, St. Josephs Hospital, Phoenix, Ariz.). The brain tissue was weighed on ice and 4 volumes of homogenization buffer (50 mM Tris-HCL, 10 mM EDTA pH 7.5) with 1% SDS was added followed by sonication of the samples. A 1/100 dilution of the protease inhibitor cocktail (Halt Protease inhibitor, Pierce) was added and the samples were centrifuged at 13,000 rpm long enough to remove any insoluble material (typically 15-45 min at 4° C.). The resulting extracts were separated on a 10% Tris/Tricine gel followed by transfer onto a 0.2 μm nitrocellulose membrane and probed with C6 nanobody as described.

Human brain sections were generously provided by Dr. Thomas Beach (Civin Laboratory for Neuropathology, Sun Health Research Institute, Sun City, Ariz.). Brain tissue from non-diseased (ND) or Alzheimer's disease (AD) brains were homogenized and 12 μg aliquots were applied to a gridded nitrocellulose membrane as previously reported (28). Staining intensities of the blot were quantified using ImageJ software.

Results

Bio-Panning Against Naturally Derived Aβ Oligomers.

Serial negative panning performed against brain derived proteins from which Aβ has been depleted (FIG. 2A), brain-derived monomer coated mica (FIG. 2B) and 5 pieces of mica coated with synthetic Aβ monomers (FIG. 2C-E) resulted in elimination of virtually 100% of phage binding to these off-target antigens. The remaining phage aliquot from the last synthetic monomer coated mica was then added to mica coated with the brain derived SDS-stable Aβ oligomers (FIG. 2F). Approximately 400 single clones were recovered from the positive panning step.

Phage Recovered from Panning Binds Specifically to Brain Derived Oligomers.

We verified that phage recovered from the positive panning steps specifically bound SDS-stable oligomeric Aβ, but not to other, off-target antigens. Pooled phage from the approximately 400 recovered clones showed abundant binding to the brain derived Aβ oligomers, but not to monomeric Aβ or other brain derived proteins (FIG. 3).

Selection for High Affinity Phage.

To select phage with the highest affinity for oligomeric Aβ, we added an aliquot of the pooled phage from the 400 recovered clones to serial dilutions of brain derived Aβ oligomers. At low antigen concentrations, high affinity clones should preferentially bind over low affinity variants. Phage recovered from the mica samples containing 10 pg of brain derived Aβ oligomers were used for further analyses.

Production of Soluble Nanobody.

Figure 4:
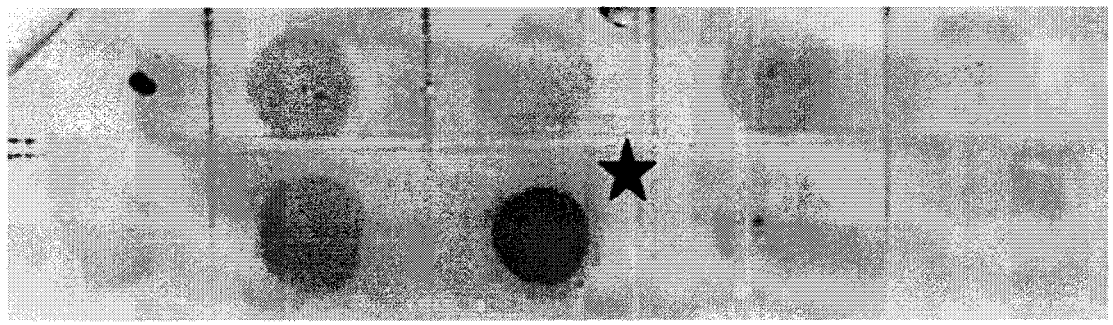
FIG. 4. Dot-blot to determine expression levels of isolated clones. Phage binding to the 10 pg brain derived dimers were eluted and transformed into Hb2151 competent cells. Single clones were picked and tested for levels of soluble scFv expression by dot blot analysis. The clone with the strongest expression (★) C6, was picked for further study.

DNA sequence analysis indicated that there were 18 distinct clones from the 30 clones recovered from the mica sample containing 10 pg of brain derived Aβ. Expression levels of the 18 clones were analyzed and clone C6 was selected for further studies based on its high expression (FIG. 4).

C6 Phage Specifically Recognizes Brain Derived Oligomers.

Figure 5A:
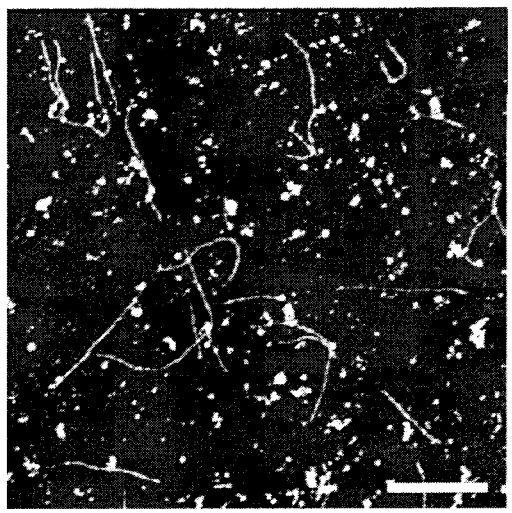
FIGS. 5A-5D. C6 specifically recognizes brain derived oligomers. Binding of C6 phage to A) natural brain derived oligomers and B) 3D synthetic Aβ aggregates was compared to binding of A4 to the same samples (C, D). Scale bar represents 1 μm.
Figure 5B:
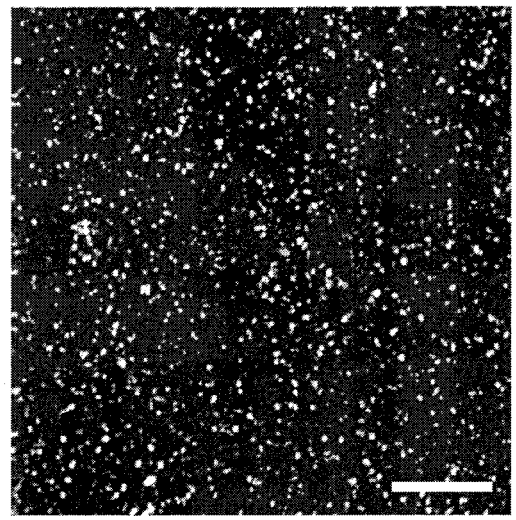
Figure 5C:
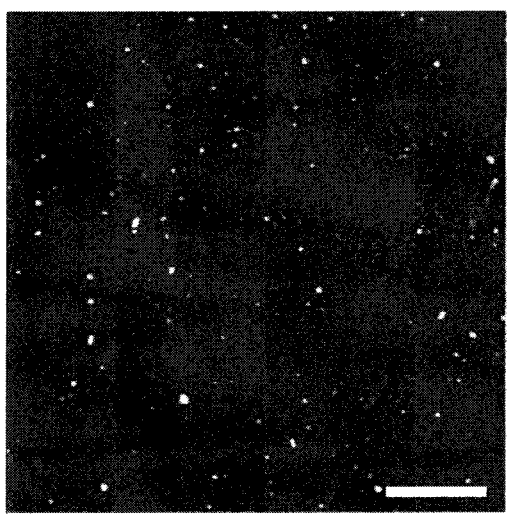
Figure 5D:
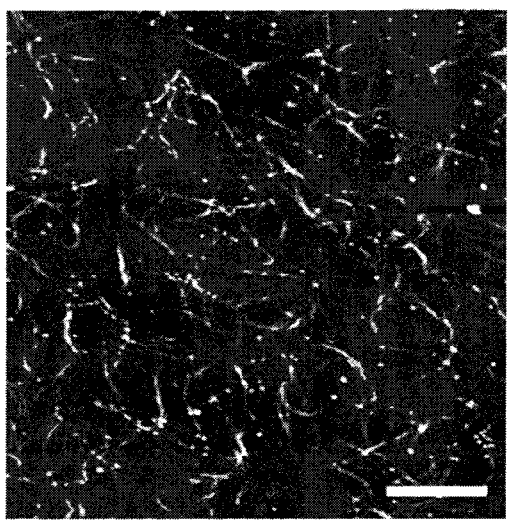

We verified that C6 phage specifically bound brain derived Aβ oligomers and did not bind other brain derived proteins or synthetic Aβ oligomers. C6 phage specifically bound natural brain derived oligomers but not synthetic Aβ aggregates corresponding to 3 days of aggregation (FIG. 5A-B). In contrast, a previously described nanobody that specifically recognized a synthetic oligomeric form of Aβ, A4, bound the 3D Aβ aggregates but did not bind the brain derived Aβ oligomers recognized by C6 (FIG. 5C-D).

Purification of C6 Nanobody.

Soluble protein from the C6 phage was expressed and purified by metal ion chromatography. Purified protein showed the expected 29 kDa band corresponding to a full length scFv (data not shown).

C6 Recognizes an Oligomeric Aβ Species Produced by 7PA2 Cells.

Figure 6:
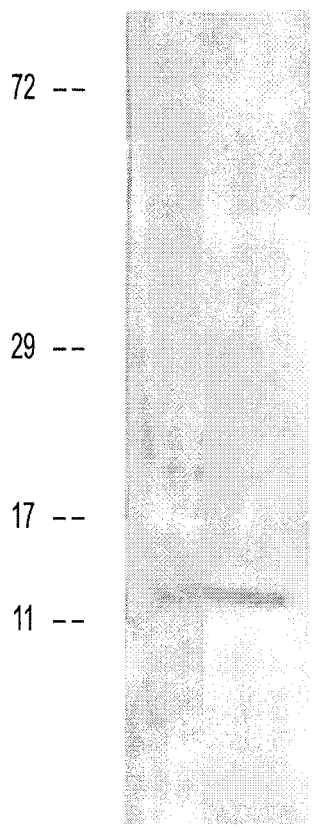
FIG. 6. C6 nanobody detects Aβ oligomers in 7PA2 cell medium. When 25 μg of the cell media was probed with C6 nanobody, a band of around 12-16 kDa could be detected, corresponding to trimeric or tetrameric morphology of Aβ.

When cell supernatant from hAPP over-expressing 7PA2 cells was analyzed by western blot probed with C6 nanobody, a 12-16 kDa band could be detected, corresponding to either an SDS-stable trimeric or tetrameric aggregate of Aβ (FIG. 6).

C6 Inhibits Aggregation of Aβ.

Figure 7:
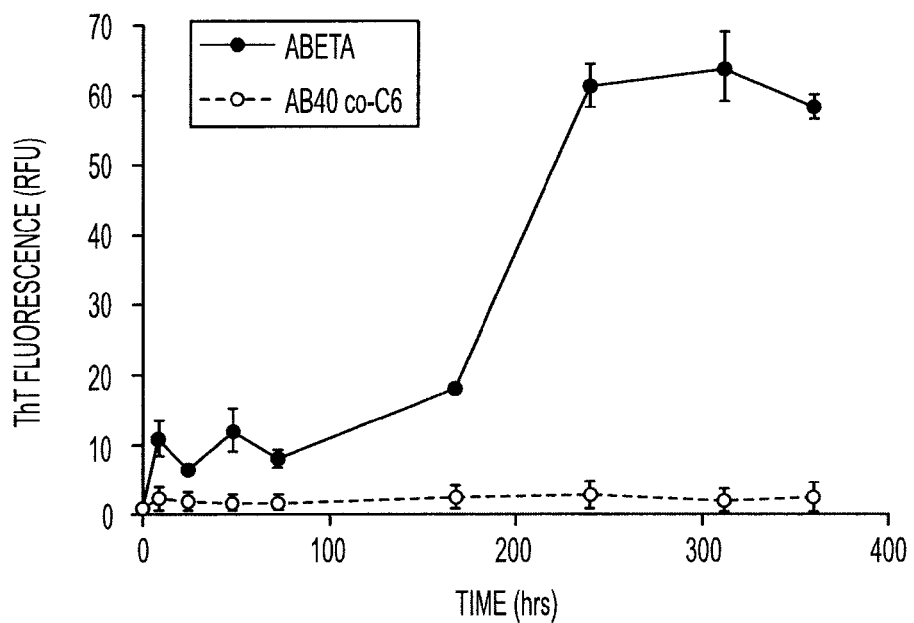
FIG. 7. ThT fluorescence assay. Aggregation of 50 μM Aβ incubated with and without 5 μM C6 was monitored by ThT fluorescence. Each experiment was performed in triplicate.
Figures 8A, 8B, 8C, 8D:
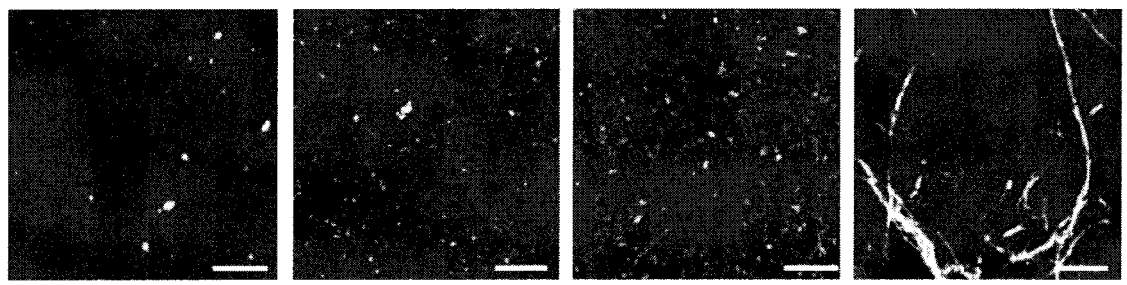
FIGS. 8A-8H. Morphology of Aβ incubated with or without C6. AFM images of 50 μM Aβ incubated without C6 for A) 0 hour, B) 3 day, C) 7 days, D) 10 days; or with C6 for E) 0 hour, F) 3 day, G) 7 days, H) 10 days. Scale bar represents 1 μm.
Figures 8E, 8F, 8G, 8H:
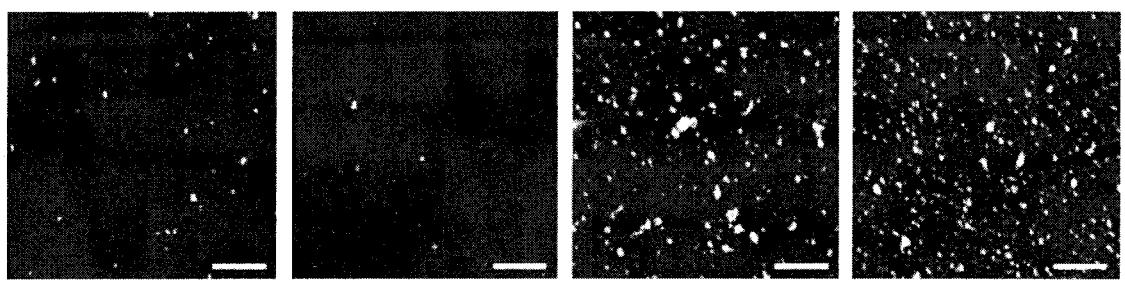

The inventors next determined whether the C6 nanobody could alter in vitro aggregation of Aβ. Incubation of Aβ alone showed a typical time-dependent increase in ThT fluorescence reaching a plateau after 10 days when fibrils are formed, while co-incubation of Aβ with C6 nanobody dramatically inhibited aggregation, as evidenced by both ThT staining (FIG. 7) and AFM analysis (FIG. 8).

Height Distribution Analyses.

To determine the size of the Aβ aggregates stabilized upon incubation with the C6 nanobody, we performed a height distribution analysis of the AFM images obtained from the samples taken at different time points with Aβ incubated alone and Aβ co-incubated with C6 nanobody. When incubated alone, Aβ aggregates show a continual increase in height with time, starting with heights <1 nm at t=0 h, presumably corresponding to monomeric Aβ, and increasing steadily with time, whereas heights >4 nm corresponding to fibrillar Aβ predominate after 7 days (Table 1A). In contrast, when Aβ is co-incubated with C6 nanobody, the aggregation rate of Aβ is dramatically altered, with particle heights remaining essentially constant with the vast majority of particles having heights between 2-3 nm, even after 7 days of aggregation (Table 1B).

Table 1 Aβ40 incubated alone (A) or co-incubated with 5 μM C6 nanobody (B) for 8 days. Height distribution analysis of AFM samples was performed using SPIP software. Percentages corresponding to highest occurrences for each time point are indicated in bold.

TABLE 1

| Heights | 0 hr | 1 day | 2 d | 3 d | 5 d | 8 d |
|---|---|---|---|---|---|---|
| A. Aβ40 Alone | | | | | | |
| <1 nm | 98.7 | 0.8 | 0 | 0.1 | 0 | 0 |
| 1-2 nm | 1.3 | 76.2 | 2.8 | 4.5 | 0.9 | 0.1 |
| 2-3 nm | 0 | 21.8 | 92.5 | 82.4 | 17.2 | 0.3 |
| 3-4 nm | 0 | 0.9 | 3.4 | 11.7 | 69.5 | 4.8 |
| >4 nm | 0 | 0.3 | 1.3 | 1.3 | 12.4 | 94.8 |
| B. Aβ40 co-incubated with C6 | | | | | | |
| 0-1 nm | | 43.6 | 10.8 | 0.1 | 0.4 | 0.1 |
| 1-2 nm | | 26.2 | 36.3 | 6.0 | 19.6 | 39.2 |
| 2-3 nm | | 14.2 | 25.5 | 56.8 | 77.4 | 59.6 |
| 3-4 nm | | 6.5 | 22.1 | 34.3 | 2.0 | 0.8 |
| >4 nm | | 9.5 | 5.3 | 2.8 | 0.6 | 0.2 |

Figures 9A, 9B:
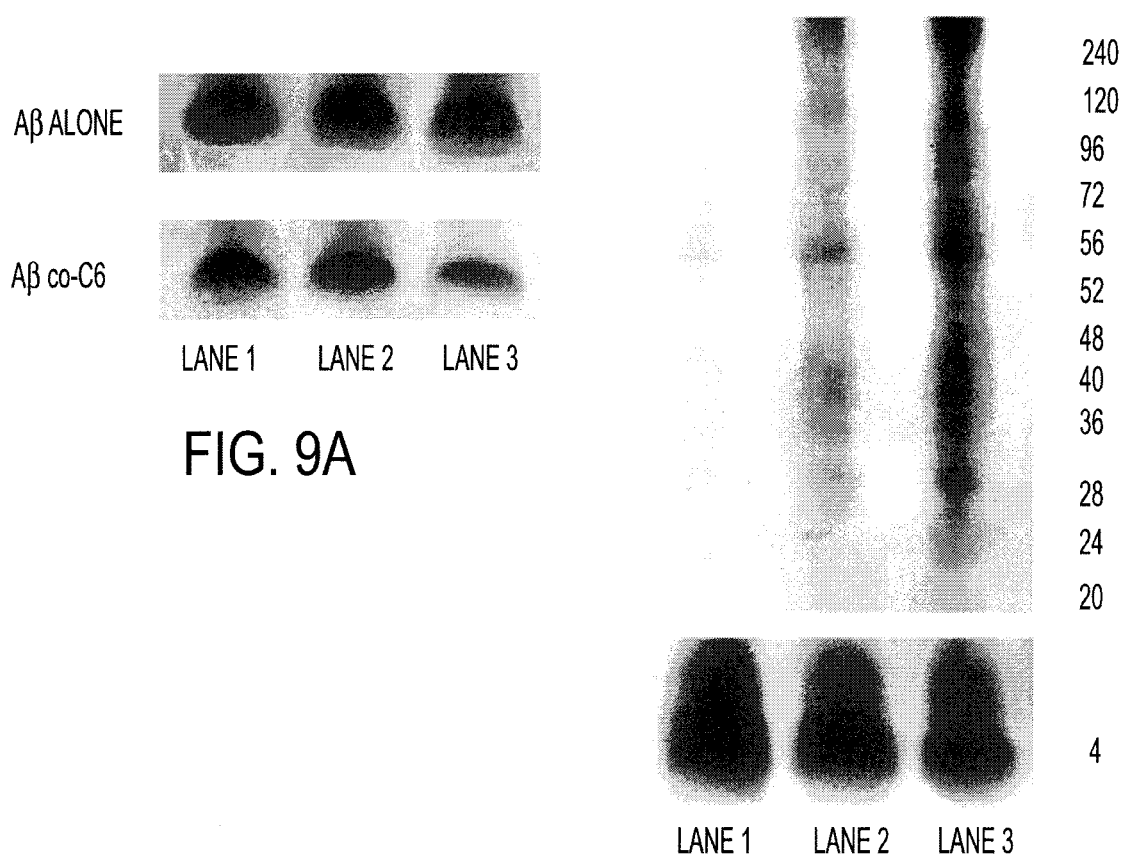
FIGS. 9A-9B: C6 stabilizes SDS-stable oligomers. 50 μM Aβ was incubated alone or in the presence of 5 μM C6 nanobody. Aliquots corresponding to monomers (Lane 1), early oligomers corresponding to 3 h-1D of aggregation (Lane 2) and late stage oligomers corresponding to 2-4D of aggregation (Lane 3) were separated on a 10% Tris-Tricine gel followed by transfer onto a nitrocellulose membrane. The membrane was probed with 1/1000 dilution of 6E10 monoclonal antibody followed by 1/1000 dilution of goat anti-mouse IgG-HRP secondary antibody. A) Comparison of Aβ monomer levels when incubated with or without C6. B) Depletion of monomers and appearance of SDS stable oligomers when Aβ is incubated with C6.

Since the in vitro Aβ aggregates are not SDS-stable, when the Aβ samples corresponding to different time points of aggregation are separated on a 10% Tris/Tricine gel containing SDS, all lanes showed a strong band corresponding to monomeric Aβ (FIG. 9A). However, when the Aβ samples were incubated with C6 nanobody a distinct reduction in monomeric Aβ levels was observed with time (FIG. 9A). Low intensity bands corresponding to Aβ aggregates of sizes 28 kD, 40 kD and 56 kD could be observed (FIG. 9B) indicating that co-incubation with C6 generates SDS-stable oligomers similar to the oligomers generated in vivo.

Effect of C6 Nanobodies on Aβ Induced Cytotoxicity Towards SH-SY5Y Neuroblastoma Cells.

Figure 10:
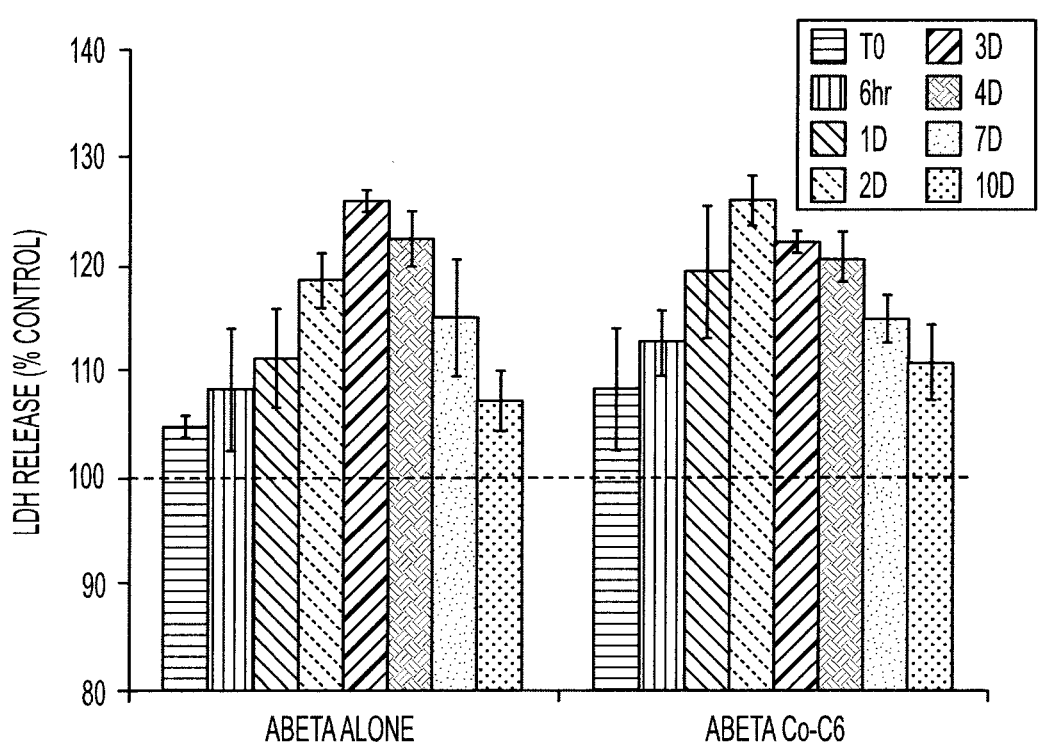
FIG. 10. C6 stabilizes toxic oligomeric form of Aβ. Co-incubation of 50 μM Aβ with 5 μM C6 maintains Aβ-induced toxicity towards SH-SY5Y human neuroblastoma cells. The final concentrations of Aβ and C6 nanobody added to the cells were 1 μM and 0.1 μM respectively. The error bars indicate SEM. Line at 100% indicates cells incubated with buffer alone.

Since C6 nanobody blocks aggregation of Aβ into fibrils, but stabilizes the formation of an oligomeric species, we determined whether C6 nanobody alters cytotoxicity of Aβ aggregates toward a SH-SY5Y neuroblastoma cell line. Cells treated with Aβ alone showed an expected increase in toxicity when incubated with oligomeric Aβ, with peak toxicity observed at 3 and 4 days of aggregation when 2-3 nm oligomeric Aβ concentration are highest (FIG. 10). As the particle height increased upon further aggregation into proto-fibrils and fibrils after 7 and 10 days, a reduction in toxicity was observed. Incubation of cells with the Aβ samples co-incubated with C6 nanobody showed similar toxic effects, with toxicity slightly increasing at earlier time points suggesting that the 2-3 nm aggregate species stabilized by incubating Aβ with C6 nanobody are toxic to the neuronal cell line (FIG. 10).

C6 Nanobody Recognizes Aβ Aggregates in Brain Tissue.

To determine whether C6 nanobody could also recognize small oligomeric Aβ aggregates in brain tissue, we tested different age mouse brain tissue from wild type and triple transgenic (3xTg) mice developed by LaFerla et al. (34). Brain extracts from Aβ over-expressing transgenic mice (Tg2576) and control mice were homogenized and run on a 10% Tris-Tricine gel, and transferred onto a nitro-cellulose membrane for western blot analysis. The membrane was probed with C6 nanobody using a 9E10-biotin primary and streptavidin-HRP as secondary antibody and stained with DAB (Sigma). Staining intensity of bands corresponding to 40 kDa was quantified using ImageJ software and compared to the background. Samples with standard deviation a) <2 times background are denoted as −; b) 2-3 times background as +; and c) 3-4 times background as ++ and d) >4 times background as +++. Thus, when the tissues were probed with C6 nanobody, strong reactivity was observed with 22 and 27 weeks old 3xTg samples, while little or no binding was observed with similar aged mice or 68.4 week 3xTg mice (Table 2).

TABLE 2

C6 reactivity with mouse brain samples

| Mouse Type | Age | Reactivity |
|---|---|---|
| Wild Type | 22 wks | − |
| Wild Type | 28.7 wks | − |
| Transgenic | 10 wks | ++ |
| Transgenic | 22 wks | +++ |
| Transgenic | 27.3 wks | +++ |
| Transgenic | 68.4 wks | + |

Next, the C6 antibody fragment was reacted with blotted aliquots of soluble homogenized samples obtained from healthy (ND) or AD human brain tissue. Brain extracts from the medial temporal gyrus of Non Diseased patients (ND) and Alzheimer's Disease patients (AD) were homogenized and deposited onto a nitrocellulose membrane and probed with C6 nanobody. Staining intensity of the dot blot was quantified using ImageJ software and compared to the background. Samples with standard deviation a) <2 times background are denoted as −; b) 2-3 times background as +; and c) 3-4 times background as ++ and d) >4 times background as +++. Thus, C6 reacted strongly with brain tissue from AD patients who had moderate plaque frequency, but showed little or no reaction with brain tissue from AD patients with severe plaques or with the ND patients (Table 3).

TABLE 3

C6 reactivity with human brain samples

| Sample | Sample Description | Reactivity |
|---|---|---|
| ND1 | No plaque | − |
| ND2 | No plaque | − |
| ND3 | No plaque | + |
| ND4 | Moderate Frequency Plaque | − |
| ND5 | Moderate Frequency Plaque | − |
| ND6 | Moderate Frequency Plaque | + |
| AD1 | Moderate Frequency Plaque | ++ |
| AD2 | Moderate Frequency Plaque | +++ |
| AD3 | Moderate Frequency Plaque | ++ |
| AD4 | Severe Plaques | + |
| AD5 | Severe Plaques | − |
| AD6 | Severe Plaques | − |

Discussion

According to the amyloid cascade hypothesis, neuronal death in AD is a consequence of accumulation and deposition of Aβ which could result either from its over-production or reduced clearance (35). Fibrillar forms of Aβ are the major pathological features of AD, and were initially thought to be responsible for neurodegeneration (36-37). However, numerous studies implicate small soluble Aβ aggregates as the relevant toxic species. For example passive immunization of transgenic mouse models with antibodies against Aβ showed recovery of memory loss without reduction of amyloid plaque burden (23-24). SDS-stable Aβ dimers and trimers were extracted in the soluble fraction from human AD brain and extracts of amyloid plaques (38-41). These low-n SDS-stable Aβ oligomers were implicated in the inhibition of hippocampal LTP in rats (18), impairment of short term memory (19), affected the dendritic morphology in neuronal cells by causing synaptic losses (20) and correlated strongly with dementia in AD patients (14). These studies suggest that these low-n SDS-stable Aβ oligomers are involved in AD, and reagents that recognize this Aβ aggregate species can be valuable therapeutic and diagnostic tools.

Single chain variable domain (scFv) antibodies represent a therapeutic approach that can avoid the inflammatory responses seen with conventional antibodies and can be selected to have specificity for target morphologies. The inventors previously developed a novel bio-panning technique combining atomic force microscopy and phage display technology (25) that enabled isolation of antibody fragments against specific morphologies of Aβ (28). The bio-panning was performed against synthetic Aβ oligomers generated in vitro. In order to isolate antibody fragments against the synapto-toxic naturally derived low-n SDS-stable Aβ oligomers, the panning protocol (FIG. 1) was modified since the brain derived oligomeric Aβ aggregates were available only in very limited amounts (nanograms) and were enriched but not purified.

We included several negative panning steps to eliminate phage binding to off-target antigens. Negative panning was performed against brain derived proteins and monomeric Aβ, and also against synthetic Aβ. The negative panning steps enabled us to eliminate virtually all phage bound to off-target antigens, and allowed for isolation of phage that bind specifically to the brain derived oligomers using minimal target sample (FIG. 2). After a single round of positive panning, we isolated approximately 400 clones from a starting phage library of $10^{12}$ clones. Phage from each of the 400 clones was independently amplified to enable phage from all the clones to amplify to the same extent, then pooled and assayed to verify specificity for the target antigen, and was observed to bind specifically to the target antigen (FIG. 3).

Since availability of antigen was limited, we modified the screening protocol to facilitate isolation of high affinity clones. At low antigen concentrations, phage will compete for antigen sites and high affinity phage will preferentially bind over low affinity clones. The high affinity screen resulted in identification of 18 unique sequences. Further selection of these 18 clones was based on protein expression levels; identifying the C6 clone for further studies (FIG. 4).

Specificity of the C6 phage for the brain derived Aβ oligomers (but not off-target antigens or synthetic Aβ oligomers) was verified by AFM (FIG. 5). We previously identified a nanobody, A4, that specifically recognized oligomeric Aβ species generated in vitro (28). Here we show that the brain derived SDS-stable Aβ oligomers recognized by the C6 nanobody represents a different, conformationally distinct small soluble Aβ aggregate species. All these aggregate species are present selectively in human AD brain tissue (13, 28) indicating that these are a variety of different Aβ aggregate species generated in human tissue and that there may be multiple toxic species and mechanisms.

When incubated with monomeric Aβ, the C6 nanobody inhibits fibril formation (FIG. 7, 8) but shifts the equilibrium from larger to smaller oligomers, stabilizing formation of a 2-3 nm Aβ oligomeric aggregate (Table 1) which was significantly toxic to neuroblastoma cells (FIG. 10). The Aβ oligomers generated in the presence of C6 nanobodies are SDS-stable (FIG. 9), similar to the brain derived Aβ oligomers, suggesting that the small low-n SDS-stable oligomers in the brain are potentially being generated by interacting with certain brain proteins similar to the C6 nanobody. This ability of C6 nanobodies to generate SDS-stable oligomers is uniquely different from other oligomer Aβ specific antibodies which have been previously described by our group.

Western blot analysis revealed that the C6 nanobody recognized a 12-16 kDa Aβ oligomeric species produced by the 7PA2 cell line that over-expressed hAPP (FIG. 6) indicating that C6 nanobody recognized a trimeric or tetrameric form of naturally derived SDS-stable Aβ. Further, height distribution analysis revealed that the size of the oligomeric species recognized by the C6 nanobody in FIG. 5A was 2.1 nm, corresponding to the height of a photo-cross-linked tetrameric form of Aβ (42). These results, together with the western blot in FIG. 9 indicated that the small, SDS-stable, low-n oligomeric morphology of Aβ recognized by the C6 nanobody was a tetramer.

C6 nanobodies could also recognize Aβ in the brain tissue of 3xTg mouse models of AD, as well from AD brain patients. When used to probe brain extracts from ND and AD patients, C6 nanobodies strongly reacted with extracts from AD patients diagnosed with moderate frequency plaques, but not with extracts from AD patients with severe plaques or with extracts from ND patients. These results indicate that morphology-specific and protein-specific reagent C6 nanobody can differentiate which protein aggregate species are involved in different stages of disease. Reagents such as the C6 nanobody can be very useful tools to more accurately diagnose neurodegenerative diseases and may help to monitor progression and treatment of AD.

Here we demonstrated that a novel bio-panning protocol could effectively be used to isolate nanobodies against specific protein morphologies even when the target antigen was only available in trace amounts and could not be purified. The results indicate there are multiple different morphologically distinct oligomeric Aβ species that naturally occur in human tissue and that they can have distinctly different cytotoxicity effects. Such highly selective morphology specific reagents represent powerful tools that have important diagnostic and therapeutic applications for neurodegenerative diseases.

Antibody-Mediated Clearance

Another approach to clear Aβ from the brain that has received extensive coverage because of its promising early results is antibody mediated clearance or immunization. Immunization of transgenic AD mice with aggregated Aβ was shown to delay deposition of Aβ and also to clear Aβ deposits already present in the brain (Schenk, D., et al. (1999). *Nature* 400: 173-177). Passive immunization of these same mice by periodic injection of antibodies generated against Aβ was also shown to delay deposition of Aβ and reduce Aβ deposits that were already present (Bard, F., et al. (2000). *Nat Med* 6: 916-9). The clearance of Aβ deposits from brain tissue in an ex vivo assay was correlated with Fc receptor mediated phagocytosis (Bard, F., et al. (2000). *Nat Med* 6: 916-9). Behavior studies of mice that were immunized against Aβ also showed reduced memory loss and behavioral impairment (Janus, C., et al. (2000). *Nature* 408: 979-82; Morgan, D., et al. (2000). *Nature* 408: 982-5). In human AD patients, active immunization against aggregated Aβ decreased cognitive decline (Hock, C., et al. (2003). *Neuron* 38: 547-554) and reduced neuritic pathology (Nicoll, J. A., D. Wilkinson, C. Holmes, P. Steart, H. Markham and R. O. Weller (2003). *Nat Med* 9: 448-52), although the study had to be suspended due to occurrence of aseptic meningoencephalitis (Check, E. (2002). *Nature* 415: 462; Schenk, D. (2002). *Nat Rev Neurosci* 3: 824-8; Orgogozo, J. M., et al. (2003). *Neurology* 61: 46-54). Despite cancellation of the immunization trials, these studies provide powerful evidence that clearance of Aβ can be a viable therapeutic approach for treating AD providing the inflammatory response can be controlled. There is considerable evidence that AD is an inflammatory disease (reviewed in (Akiyama, H., et al. (2000). *Neurobiol Aging* 21: 383-421)), and antibody mediated clearance by phagocytosis may exacerbate brain inflammation and damage (Check, E.

(2002). *Nature* 415: 462; Schenk, D. (2002). *Nat Rev Neurosci* 3: 824-8; Orgogozo, J. M., et al. (2003). *Neurology* 61: 46-54). In order to avoid potentially damaging inflammatory responses in the brain associated with immunotherapeutic approaches, single chain variable domain antibody fragments (nanobodies) which contain only the variable heavy and light chain regions represent a promising alternative to antibodies since they do not contain the Fc region (Miller, T. W. and A. Messer (2005). *Mol Ther* 12: 394-401).

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Hardy, J., and Selkoe, D. J. (2002) The amyloid hypothesis of Alzheimer's disease: progress and problems on the road to therapeutics, Science 297, 353-356.
2. Kang, J., Lemaire, H. G., Unterbeck, A., Salbaum, J. M., Masters, C. L., Grzeschik, K. H., Multhaup, G., Beyreuther, K., and Muller-Hill, B. (1987) The precursor of Alzheimer's disease amyloid A4 protein resembles a cell-surface receptor., Nature 325, 733-736.
3. Golde, T. E., Estus, S., Younkin, L. H., Selkoe, D. J., and S. G., Y. (1992) Processing of the Amyloid Protein Precursor to Potentially Amyloidogenic Derivatives, Science 255, 728-730.
4. Estus, S., Golde, T. E., Kunishita, T., Blades, D., Lowery, D., Eisen, M., Usiak, M., Qu, X., Tabira, T., Greenberg, B. D., and Younkin, S. G. (1992) Potentially Amyloidogenic, Carboxyl-Terminal Derivatives of the Amyloid Protein Precursor, Science 255, 726-728.
5. Yankner, B. A. (1996) Mechanisms of Neuronal Degeneration in Alzheimer's Disease., Neuron 16, 921-923.
6. Harper, J. D., and Lansbury, P. T. J. (1997) Models of amyloid seeding in Alzheimer's disease and Scrapie: mechanistic truths and physiological consequences of the time-dependent solubility of amyloid proteins, Annu. Rev. Biochem. 66, 385-407.
7. Harper, J. D., Wong, S. S., Lieber, C. M., and Lansbury, P. T. J. (1997) Observation of metastable AB amyloid protofibrils by atomic force microscopy, Chemistry & Biology 4, 119-125.
8. Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A., and Klein, W. L. (1998) Diffusible, nonfibrillar ligands derived from Abeta1-42 are potent central nervous system neurotoxins, Proc Natl Acad Sci USA 95, 6448-6453.
9. Caughey, B., and Lansbury, P. T. (2003) Protofibrils, pores, fibrils, and neurodegeneration: separating the responsible protein aggregates from the innocent bystanders, Annu Rev Neurosci 26, 267-298.
10. Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A., and Klein, W. L. (1998) Diffusible, nonfibrillar ligands derived from Abeta1-42 are potent central nervous system neurotoxins, Proc Natl Acad Sci USA 95, 6448-6453.
11. Gong, Y., Chang, L., Viola, K. L., Lacor, P. N., Lambert, M. P., Finch, C. E., Krafft, G. A., and Klein, W. L. (2003) Alzheimer's disease-affected brain: presence of oligomeric A beta ligands (ADDLs) suggests a molecular basis for reversible memory loss, Proc Natl Acad Sci USA 100, 10417-10422.
12. Zameer, A., Schulz, P., Wang, M. S., and Sierks, M. R. (2006) Single chain Fv antibodies against the 25-35 Abeta fragment inhibit aggregation and toxicity of Abeta42, Biochemistry 45, 11532-11539.
13. Shankar, G. M., Li, S., Mehta, T. H., Garcia-Munoz, A., Shepardson, N. E., Smith, I., Brett, F. M., Farrell, M. A., Rowan, M. J., Lernere, C. A., Regan, C. M., Walsh, D. M., Sabatini, B. L., and Selkoe, D. J. (2008) Amyloid-beta protein dimers isolated directly from Alzheimer's brains impair synaptic plasticity and memory, Nat Med 14, 837-842.
14. Mc Donald, J. M., Savva, G. M., Brayne, C., Welzel, A. T., Forster, G., Shankar, G. M., Selkoe, D. J., Ince, P. G., and Walsh, D. M. (2010) The presence of sodium dodecyl sulphate-stable Abeta dimers is strongly associated with Alzheimer-type dementia, Brain 133, 1328-1341.
15. Walsh, D. M., Tseng, B. P., Rydel, R. E., Podlisny, M. B., and Selkoe, D. J. (2000) The oligomerization of amyloid beta-protein begins intracellularly in cells derived from human brain, Biochemistry 39, 10831-10839.
16. Lesne, S., Koh, M. T., Kotilinek, L., Kayed, R., Glabe, C. G., Yang, A., Gallagher, M., and Ashe, K. H. (2006) A 17. Kawarabayashi, T., Shoji, M., Younkin, L. H., Wen-Lang, L., Dickson, D. W., Murakami, T., Matsubara, E., Abe, K., Ashe, K. H., and Younkin, S. G. (2004) Dimeric amyloid beta protein rapidly accumulates in lipid rafts followed by apolipoprotein E and phosphorylated tau accumulation in the Tg2576 mouse model of Alzheimer's disease, J Neurosci 24, 3801-3809.

18. Walsh, D. M., Klyubin, I., Fadeeva, J. V., Cullen, W. K., Anwyl, R., Wolfe, M. S., Rowan, M. J., and Selkoe, D. J. (2002) Naturally secreted oligomers of amyloid beta protein potently inhibit hippocampal long-term potentiation in vivo, Nature 416, 535-539.

19. Cleary, J. P., Walsh, D. M., Hofmeister, J. J., Shankar, G. M., Kuskowski, M. A., Selkoe, D. J., and Ashe, K. H. (2005) Natural oligomers of the amyloid-beta protein specifically disrupt cognitive function, Nat Neurosci 8, 79-84.

20. Shankar, G. M., Bloodgood, B. L., Townsend, M., Walsh, D. M., Selkoe, D. J., and Sabatini, B. L. (2007) Natural oligomers of the Alzheimer amyloid-beta protein induce reversible synapse loss by modulating an NMDA-type glutamate receptor-dependent signaling pathway, J Neurosci 27, 2866-2875.

21. O'Hare, E., Weldon, D. T., Mantyh, P. W., Ghilardi, J. R., Finke, M. P., Kuskowski, M. A., Maggio, J. E., Shephard, R. A., and Cleary, J. (1999) Delayed behavioral effects following intrahippocampal injection of aggregated A beta (1-42), Brain Res 815, 1-10.

22. Cleary, J., Hittner, J. M., Semotuk, M., Mantyh, P., and O'Hare, E. (1995) Beta-amyloid (1-40) effects on behavior and memory, Brain Res 682, 69-74.

23. Dodart, J. C., Bales, K. R., Gannon, K. S., Greene, S. J., DeMattos, R. B., Mathis, C., DeLong, C. A., Wu, S., Wu, X., Holtzman, D. M., and Paul, S. M. (2002) Immunization reverses memory deficits without reducing brain Abeta burden in Alzheimer's disease model, Nat Neurosci 5, 452-457.

24. Kotilinek, L. A., Bacskai, B., Westerman, M., Kawarabayashi, T., Younkin, L., Hyman, B. T., Younkin, S., and Ashe, K. H. (2002) Reversible memory loss in a mouse transgenic model of Alzheimer's disease, J Neurosci 22, 6331-6335.

25. Barkhordarian, H., Emadi, S., Schulz, P., and Sierks, M. R. (2006) Isolating recombinant antibodies against specific protein morphologies using atomic force microscopy and phage display technologies, Protein Eng Des Sel 19, 497-502.

26. Emadi, S., Barkhordarian, H., Wang, M. S., Schulz, P., and Sierks, M. R. (2007) Isolation of a human single chain antibody fragment against oligomeric alpha-synuclein that inhibits aggregation and prevents alpha-synuclein-induced toxicity, J Mol Biol 368, 1132-1144.

27. Emadi, S., Kasturirangan, S., Wang, M. S., Schulz, P., and Sierks, M. R. (2009) Detecting morphologically distinct oligomeric forms of alpha-synuclein, J Biol Chem 284, 11048-11058.

28. Zameer, A., Kasturirangan, S., Emadi, S., Nimmagadda, S. V., and Sierks, M. R. (2008) Anti-oligomeric Abeta single-chain variable domain antibody blocks Abeta-induced toxicity against human neuroblastoma cells, J Mol Biol 384, 917-928.

29. Sheets, M. D., Amersdorfer, P., Finnern, R., Sargent, P., Lindquist, E., Schier, R., Hemingsen, G., Wong, C., Gerhart, J. C., and Marks, J. D. (1998) Efficient construction of a large nonimmune phage antibody library: the production of high-affinity human single-chain antibodies to protein antigens, Proc Natl Acad Sci USA 95, 6157-6162.

30. Marks, J. D., Hoogenboom, H. R., Bonnert, T. P., McCafferty, J., Griffiths, A. D., and Winter, G. (1991) By-passing immunization. Human antibodies from V-gene libraries displayed on phage, J Mol Biol 222, 581-597.

31. Wang, M. S., Zameer, A., Emadi, S., and Sierks, M. R. (2009) Characterizing antibody specificity to different protein morphologies by AFM, Langmuir 25, 912-918.

32. Liu, R., Yuan, B., Emadi, S., Zameer, A., Schulz, P., McAllister, C., Lyubchenko, Y., Goud, G., and Sierks, M. R. (2004) Single chain variable fragments against beta-amyloid (Abeta) can inhibit Abeta aggregation and prevent abeta-induced neurotoxicity, Biochemistry 43, 6959-6967.

33. Legrand, C., Bour, J. M., Jacob, C., Capiaumont, J., Martial, A., Marc, A., Wudtke, M., Kretzmer, G., Demangel, C., Duval, D., and et al. (1992) Lactate dehydrogenase (LDH) activity of the cultured eukaryotic cells as marker of the number of dead cells in the medium [corrected], J Biotechnol 25, 231-243.

34. Oddo, S., Caccamo, A., Shepherd, J. D., Murphy, M. P., Golde, T. E., Kayed, R., Metherate, R., Mattson, M. P., Akbari, Y., and LaFerla, F. M. (2003) Triple-transgenic model of Alzheimer's disease with plaques and tangles: intracellular Abeta and synaptic dysfunction, Neuron 39, 409-421.

35. Hardy, J. A., and Higgins, G. A. (1992) Alzheimer's disease: the amyloid cascade hypothesis, Science 256, 184-185.

36. Lorenzo, A., and Yankner, B. A. (1994) Beta-amyloid neurotoxicity requires fibril formation and is inhibited by congo red, Proc Natl Acad Sci USA 91, 12243-12247.

37. Pike, C. J., Burdick, D., Walencewicz, A. J., Glabe, C. G., and Cotman, C. W. (1993) Neurodegeneration induced by beta-amyloid peptides in vitro: the role of peptide assembly state, J Neurosci 13, 1676-1687.

38. McLean, C. A., Cherny, R. A., Fraser, F. W., Fuller, S. J., Smith, M. J., Beyreuther, K., Bush, A. I., and Masters, C. L. (1999) Soluble pool of Abeta amyloid as a determinant of severity of neurodegeneration in Alzheimer's disease, Ann Neurol 46, 860-866.

39. Enya, M., Morishima-Kawashima, M., Yoshimura, M., Shinkai, Y., Kusui, K., Khan, K., Games, D., Schenk, D., Sugihara, S., Yamaguchi, H., and Ihara, Y. (1999) Appearance of sodium dodecyl sulfate-stable amyloid beta-protein (Abeta) dimer in the cortex during aging, Am J Pathol 154, 271-279.

40. Funato, H., Enya, M., Yoshimura, M., Morishima-Kawashima, M., and Ihara, Y. (1999) Presence of sodium dodecyl sulfate-stable amyloid beta-protein dimers in the hippocampus CA1 not exhibiting neurofibrillary tangle formation, Am J Pathol 155, 23-28.

41. Roher, A. E., Chaney, M. O., Kuo, Y. M., Webster, S. D., Stine, W. B., Haverkamp, L. J., Woods, A. S., Cotter, R. J., Tuohy, J. M., Krafft, G. A., Bonnell, B. S., and Emmerling, M. R. (1996) Morphology and toxicity of Abeta-(1-42) dimer derived from neuritic and vascular amyloid deposits of Alzheimer's disease, J Biol Chem 271, 20631-20635.

42. Ono, K., Condron, M. M., and Teplow, D. B. (2009) Structure-neurotoxicity relationships of amyloid beta-protein oligomers, Proc Natl Acad Sci USA 106, 14745-14750.

The invention claimed is:

1. A composition comprising trimeric or tetrameric aggregates of Aβ that are SDS-stable and that are specifically bound by an antibody fragment that comprises SEQ ID NO: 1 or amino acid residues 16-292 of SEQ ID NO:1.

2. The composition of claim 1, wherein the aggregate of Aβ is conjugated to or admixed with, or both, to at least one carrier.

3. The composition of claim 2, wherein the Aβ aggregate is covalently-coupled to the carrier.

4. The composition of claim 2, wherein the carrier is an immunogenic carrier and/or an adjuvant.

5. The composition of claim 2, wherein the immunogenic carrier and/or adjuvant is bovine serum albumin, immunoglobulin, thyroglobulin, ovalbumin, tetanus toxoid, keyhold limpet hemocyanin, or a lipid moiety.

6. The composition of claim 1, further comprising a pharmaceutically acceptable vehicle.

7. The composition of claim 1, wherein the antibody fragment is immunogenic.

8. The composition of claim 1, wherein said aggregate of Aβ is a 12-16 kDa oligomeric species of Aβ that is stable in the presence of SDS.

9. The method of claim 1, wherein said composition further comprises an adjuvant.

10. A method of preparing an immunogenic Aβ aggregate comprising:
   a. contacting monomers of Aβ with an antibody fragment to form Aβ aggregates, wherein the antibody fragment comprises SEQ ID NO:1 or amino acid residues 16-292 of SEQ ID NO:1; and
   b. isolating the Aβ aggregates, wherein the Aβ aggregates comprise a trimeric or tetrameric aggregates of Aβ that are at least partially resistant to denaturation by SDS.

11. The method of claim 10, wherein the antibody fragment comprises amino acid residues 26-292 of SEQ ID NO:1.

12. A composition comprising an SDS-stable trimeric or tetrameric aggregate of Aβ that is at least partially resistant to denaturation by SDS, wherein the composition is prepared according to the method of claim 10.

* * * * *